US012369777B2

(12) United States Patent
Sharon et al.

(10) Patent No.: US 12,369,777 B2
(45) Date of Patent: Jul. 29, 2025

(54) MODULAR ROBOTIC SYSTEM FOR DRIVING MOVEMENT OF SURGICAL TOOLS

(71) Applicants:Microbot Medical Ltd., Yokneam Illit (IL); Technion Research & Development Foundation Limited, Haifa (IL)

(72) Inventors: Simon Sharon, Zichron Yaacov (IL); Idan Boader, Carmiel (IL); Evgeny Kofman, Kiriat-Motzkin (IL); Eran Cohen, Kiryat-Tivon (IL); Eyal Morag, Tel Aviv (IL); Harel Gadot, Hingham, MA (US); Moshe Shoham, Haifa (IL)

(73) Assignees: Microbot Medical Ltd., Yokneam Illit (IL); Technion Research & Development Foundation Limited, Haifa (IL)

( * ) Notice: Subject to any disclaimer, the term of this patent is extended or adjusted under 35 U.S.C. 154(b) by 170 days.

(21) Appl. No.: 17/780,039

(22) PCT Filed: Nov. 26, 2020

(86) PCT No.: PCT/IL2020/051224
§ 371 (c)(1),
(2) Date: May 26, 2022

(87) PCT Pub. No.: WO2021/105997
PCT Pub. Date: Jun. 3, 2021

(65) Prior Publication Data
US 2023/0009618 A1 Jan. 12, 2023

Related U.S. Application Data

(60) Provisional application No. 63/082,508, filed on Sep. 24, 2020, provisional application No. 62/941,842, filed on Nov. 28, 2019.

(51) Int. Cl.
*A61B 1/00* (2006.01)
*A61B 34/00* (2016.01)
(Continued)

(52) U.S. Cl.
CPC .......... *A61B 1/00147* (2013.01); *A61B 34/30* (2016.02); *A61B 34/35* (2016.02);
(Continued)

(58) Field of Classification Search
CPC ..... A61B 1/00147; A61B 34/30; A61B 34/35; A61B 34/37; A61B 34/70;
(Continued)

(56) References Cited

U.S. PATENT DOCUMENTS 3,789,841 A 2/1974 Antoshkiw
5,571,072 A 11/1996 Kronner
(Continued)

FOREIGN PATENT DOCUMENTS

CA 2918879 1/2015
CN 101918073 12/2010
(Continued)

OTHER PUBLICATIONS

Office Action Dated Jan. 11, 2024 From the Israel Patent Office Re. Application No. 297409. (6 Pages).
(Continued)

*Primary Examiner* — Richard G Louis

(57) ABSTRACT

A modular robotic surgical system comprising: a base; a plurality of tool-receivers arranged as separate units, each tool-receiver unit operable to move an elongate surgical tool received therein; a plurality of interface coupling pairs, each coupling pair comprising a first coupler as part of the base and a second coupler as part of each of the tool-receiver units; wherein each of the tool-receiver units is indepen-
(Continued)

dently and interchangeably attachable to the base via the coupling pair.

22 Claims, 22 Drawing Sheets

(51) Int. Cl.
*A61B 34/30* (2016.01)
*A61B 34/35* (2016.01)
*A61B 34/37* (2016.01)
*A61M 25/01* (2006.01)
*A61M 25/09* (2006.01)
*B25J 9/00* (2006.01)
*B25J 9/10* (2006.01)
*A61B 17/00* (2006.01)
*A61M 25/00* (2006.01)
*A61M 25/02* (2006.01)

(52) U.S. Cl.
CPC ............ *A61B 34/37* (2016.02); *A61B 34/70* (2016.02); *A61M 25/0113* (2013.01); *A61M 25/09041* (2013.01); *B25J 9/0021* (2013.01); *B25J 9/102* (2013.01); *A61B 2017/00477* (2013.01); *A61B 2034/301* (2016.02); *A61M 2025/0042* (2013.01); *A61M 2025/0253* (2013.01)

(58) Field of Classification Search
CPC .... A61B 2017/00477; A61B 2034/301; A61B 2090/062; A61M 25/0113; A61M 25/09041; A61M 2025/0042; A61M 2025/0253; B25J 9/0021; B25J 9/102
See application file for complete search history.

(56) References Cited

U.S. PATENT DOCUMENTS

| | | | |
|---|---|---|---|
| 6,017,354 A | 1/2000 | Culp et al. | |
| 6,171,234 B1 | 1/2001 | White et al. | |
| 6,290,675 B1 | 9/2001 | Vujanic et al. | |
| 6,358,199 B1 | 3/2002 | Pauker et al. | |
| 6,726,675 B1 | 4/2004 | Beyar | |
| 7,615,042 B2 | 11/2009 | Beyar et al. | |
| 8,317,745 B2 * | 11/2012 | Kirschenman | A61B 34/71 604/95.04 |
| 8,423,182 B2 | 4/2013 | Robinson et al. | |
| 8,480,618 B2 | 7/2013 | Wenderow et al. | |
| 8,894,610 B2 | 11/2014 | Macnamara et al. | |
| 9,192,745 B2 | 11/2015 | Bencteux et al. | |
| 9,795,764 B2 | 10/2017 | Pacheco et al. | |
| 10,149,680 B2 | 12/2018 | Parihar et al. | |
| 10,376,323 B2 * | 8/2019 | Farritor | A61B 90/37 |
| 10,524,867 B2 | 1/2020 | Kokish et al. | |
| 10,543,047 B2 | 1/2020 | Yu | |
| 10,820,952 B2 | 11/2020 | Yu | |
| 10,980,608 B2 | 4/2021 | Scheib et al. | |
| 2002/0133077 A1 | 9/2002 | Edwardsen et al. | |
| 2002/0177789 A1 | 11/2002 | Ferry et al. | |
| 2004/0254566 A1 | 12/2004 | Picchi et al. | |
| 2005/0021065 A1 | 1/2005 | Yamada et al. | |
| 2005/0197566 A1 | 9/2005 | Strommer et al. | |
| 2006/0041245 A1 | 2/2006 | Ferry et al. | |
| 2008/0097465 A1 | 4/2008 | Rollins et al. | |
| 2009/0247944 A1 | 10/2009 | Kirschenman et al. | |
| 2011/0028894 A1 | 2/2011 | Foley et al. | |
| 2011/0105954 A1 | 5/2011 | Cohen et al. | |
| 2011/0130718 A1 * | 6/2011 | Kidd | A61B 34/30 604/95.01 |
| 2012/0110824 A1 | 5/2012 | Smith et al. | |
| 2013/0123803 A1 | 5/2013 | Kirschenman et al. | |
| 2014/0243742 A1 | 8/2014 | Pacheco et al. | |
| 2014/0276647 A1 | 9/2014 | Yu | |
| 2014/0276935 A1 | 9/2014 | Yu | |
| 2014/0277333 A1 | 9/2014 | Lewis et al. | |
| 2014/0305993 A1 | 10/2014 | Timm et al. | |
| 2014/0309659 A1 | 10/2014 | Roh et al. | |
| 2015/0001968 A1 | 1/2015 | Zirps | |
| 2015/0094732 A1 | 4/2015 | Pacheco et al. | |
| 2015/0112362 A1 | 4/2015 | Inoue et al. | |
| 2015/0374956 A1 | 12/2015 | Bogusky | |
| 2016/0030709 A1 | 2/2016 | Losordo et al. | |
| 2016/0157941 A1 | 6/2016 | Anvari et al. | |
| 2016/0361128 A1 | 12/2016 | Seeber | |
| 2017/0105804 A1 * | 4/2017 | Yu | A61M 25/0113 |
| 2018/0055588 A1 | 3/2018 | Yanagihara et al. | |
| 2018/0228557 A1 | 8/2018 | Darisse et al. | |
| 2019/0125397 A1 | 5/2019 | Arnold et al. | |
| 2019/0201120 A1 | 7/2019 | Shelton, IV et al. | |
| 2019/0223967 A1 | 7/2019 | Abbott et al. | |
| 2019/0328599 A1 | 10/2019 | Mahoney | |
| 2020/0146759 A1 | 5/2020 | Schena et al. | |
| 2020/0155245 A1 | 5/2020 | Yu | |
| 2020/0163726 A1 | 5/2020 | Tanner et al. | |
| 2020/0222668 A1 | 7/2020 | Wenderow et al. | |
| 2020/0281666 A1 | 9/2020 | Gunn et al. | |
| 2021/0236217 A1 | 8/2021 | Sharon et al. | |
| 2021/0251709 A1 | 8/2021 | Sharon et al. | |
| 2021/0282875 A1 | 9/2021 | Sharon et al. | |
| 2022/0071723 A1 | 3/2022 | Sharon et al. | |
| 2023/0346495 A1 | 11/2023 | Sharon et al. | |
| 2024/0197415 A1 | 6/2024 | Sharon et al. | |
| 2024/0358448 A1 | 10/2024 | Boader et al. | |

FOREIGN PATENT DOCUMENTS

| | | |
|---|---|---|
| CN | 103442660 | 12/2013 |
| CN | 103599585 | 2/2014 |
| DE | 102004007935 | 5/2005 |
| EP | 1061990 | 9/2004 |
| EP | 2347785 | 7/2011 |
| IL | 123646 | 5/2010 |
| IT | 201800009380 | 4/2020 |
| JP | 2002-525182 | 8/2002 |
| JP | 2006-87474 | 4/2006 |
| JP | 2010-253168 | 11/2010 |
| JP | 2011-509763 | 3/2011 |
| JP | 2011-519678 | 7/2011 |
| JP | 2015-523148 | 8/2015 |
| JP | 2017-104581 | 6/2017 |
| KR | 10-2129337 | 7/2020 |
| WO | WO 99/45994 | 9/1999 |
| WO | WO 2013/183276 | 12/2013 |
| WO | WO 2019/070696 | 4/2019 |
| WO | WO 2019/173107 | 9/2019 |
| WO | WO 2019/195841 | 10/2019 |
| WO | WO 2019/203616 | 10/2019 |
| WO | WO 2020/072543 | 4/2020 |
| WO | WO 2021/011551 | 1/2021 |
| WO | WO 2021/011554 | 1/2021 |
| WO | WO 2021/065311 | 4/2021 |
| WO | WO 2021/105997 | 6/2021 |
| WO | WO 2021/105998 | 6/2021 |
| WO | WO 2021/105999 | 6/2021 |
| WO | WO 2022/224234 | 10/2022 |
| WO | WO 2023/007478 | 2/2023 |

OTHER PUBLICATIONS

Office Action Dated Jan. 11, 2024 From the Israel Patent Office Re. Application No. 300398. (4 Pages).
Requisition Dated Dec. 19, 2023 From the Innovation, Science and Economic Development Canada, Canadian Intellectual Property Office Re. Applicaiton No. 3,159,753. (13 Pages).
International Preliminary Report on Patentability Dated Feb. 8, 2024 From the International Bureau of WIPO Re. Application No. PCT/IL2022/050756 (10 Pages).
Supplementary European Search Report and the European Search Opinion Dated Jan. 12, 2024 From the European Patent Office Re. Application No. 20892205.4. (8 Pages).

(56) References Cited

OTHER PUBLICATIONS

International Preliminary Report on Patentability Dated Nov. 2, 2023 From the International Bureau of WIPO Re. Application No. PCT/IL2022/050303 (10 Pages).
Machine Translation Dated Jul. 24, 2024 of Notification of Office Action and Search Report Dated Jul. 16, 2024 From the State Intellectual Property Office of the People's Republic of China Re. Application No. 202080086796.0. (7 Pages).
Notice of Reason(s) for Rejection Dated Jul. 16, 2024 From the Japan Patent Office Re. Application No. 2022-530812 and Its Translation Into English. (29 Pages).
Notification of Office Action and Search Report Dated Jul. 16, 2024 From the State Intellectual Property Office of the People's Republic of China Re. Application No. 202080086796.0. (8 Pages).
Supplementary European Search Report and the European Search Opinion Dated Dec. 5, 2023 From the European Patent Office Re. Application No. 20891520.7. (11 Pages).
Official Action Dated Nov. 24, 2023 from the US Patent and Trademark Office Re. U.S. Appl. No. 17/526,060. (41 pages).
Notice of Reason(s) for Rejection Dated Jul. 23, 2024 From the Japan Patent Office Re. Application No. 2022-528230 and Its Translation Into English. (20 Pages).
Notification of Office Action and Search Report Dated May 10, 2024 From the National Intellectual Property Administration of the People's Republic of China Re. Application No. 202080092059.1 and Its Machine Translation Into English. (18 Pages).
Requisition Dated Jan. 4, 2024 From the Innovation, Science and Economic Development Canada, Canadian Intellectual Property Office Re. Application No. 3,156,099. (16 Pages).
Requisition Dated Jan. 17, 2024 From the Innovation, Science and Economic Development Canada, Canadian Intellectual Property Office Re. Application No. 3,161,864. (12 Pages).
Notice of Reasons for Rejection Dated Sep. 3, 2024 From the Japan Patent Office Re. Application No. 2022-530811. and its Translation Into English. (20 Pages).
Office Action Dated Aug. 30, 2023 From the Israel Patent Office Re. Application No. 300398. (5 Pages).
Invitation to Pay Additional Fees and Communication Relating to the Results of the Partial International Search Dated Oct. 27, 2022 From the International Searching Authority Re. Application No. PCT/IL2022/050756. (5 Pages).
Requisition Dated Aug. 15, 2024 From the Innovation, Science and Economic Development Canada, Canadian Intellectual Property Office Re. Application No. 3,159,753. (11 Pages).
International Search Report and the Written Opinion Dated Jul. 5, 2022 From the International Searching Authority Re. Application No. PCT/IL2022/050303. (19 Pages).
European Search Report and the European Search Opinion Dated Sep. 1, 2022 From the European Patent Office Re. Application No. 22168338.6. (9 Pages).
International Preliminary Report on Patentability Dated Jun. 9, 2022 From the International Bureau of WIPO Re. Application No. PCT/IL2020/051224. (10 Pages).
International Preliminary Report on Patentability Dated Jun. 9, 2022 From the International Bureau of WIPO Re. Application No. PCT/IL2020/051225. (7 Pages).
International Preliminary Report on Patentability Dated Jun. 9, 2022 From the International Bureau of WIPO Re. Application No. PCT/IL2020/051226. (11 Pages).
International Search Report and the Written Opinion Dated Feb. 15, 2021 From the International Searching Authority Re. Application No. PCT/IL2020/051224. (24 Pages).
International Search Report and the Written Opinion Dated Feb. 18, 2021 From the International Searching Authority Re. Application No. PCT/IL2020/051226. (18 Pages).
International Search Report and the Written Opinion Dated Feb. 25, 2021 From the International Searching Authority Re. Application No. PCT/IL2020/051225. (14 Pages).
Interview Summary Dated Nov. 19, 2021 from US Patent and Trademark Office Re. U.S. Appl. No. 17/233,774. (3 pages).
Interview Summary Dated Oct. 20, 2021 from US Patent and Trademark Office Re. U.S. Appl. No. 17/331,837. (2 pages).
Invitation to Pay Additional Fees and Communication Relating to the Results of the Partial International Search Dated Jan. 12, 2021 From the International Searching Authority Re. Application No. PCT/IL2020/051224. (13 Pages).
Notice of Allowance Dated Nov. 12, 2021 together with Interview Summary from the US Patent and Trademark Office Re. U.S. Appl. No. 17/331,837. (11 pages).
Notice of Allowance Dated Aug. 20, 2021 from the US Patent and Trademark Office Re. U.S. Appl. No. 17/187,936. (7 pages).
Notice of Allowance Dated Dec. 22, 2021 from US Patent and Trademark Office Re. U.S. Appl. No. 17/233,774. (12 pages).
Official Action & Interview Summary Dated Sep. 2, 2021 From the US Patent and Trademark Office Re. U.S. Appl. No. 17/233,774. (23 Pages).
Official Action Dated Aug. 2, 2021 from the US Patent and Trademark Office Re. U.S. Appl. No. 17/331,837. (19 pages).
Official Action Dated Jun. 23, 2021 From the US Patent and Trademark Office Re. U.S. Appl. No. 17/187,936. (13 Pages).
Restriction Official Action Dated Jul. 16, 2021 from the US Patent and Trademark Office Re. U.S. Appl. No. 17/233,774. (5 pages).
Office Action and Search Report Dated Jun. 4, 2023 From the Israel Patent Office Re. Application No. 298418. (10 Pages).
Requisition Dated Apr. 25, 2024 From the Innovation, Science and Economic Development Canada, Canadian Intellectual Property Office Re. Application No. 3,161,955 with claims. (10 Pages).
Supplementary European Search Report and the European Search Opinion Dated Nov. 7, 2023 From the European Patent Office Re. Application No. 20893145.1. (8 Pages).
Requisition Dated Oct. 25, 2023 From the Innovation, Science and Economic Development Canada, Canadian Intellectual Property Office Re. Application No. 3,161,955 with claims. (14 Pages).
English Summary Dated May 27, 2024 of Notification of Office Action and Search Report Dated May 10, 2024 From the National Intellectual Property Administration of the People's Republic of China Re. Application No. 202080092059.1. (2 Pages).
Notice of Allowance Dated May 30, 2024 from the US Patent and Trademark Office Re. U.S. Appl. No. 17/526,060. (5 pages).
Office Action Dated May 26, 2024 From the Israel Patent Office Re. Application No. 298418. (5 Pages).
International Search Report and the Written Opinion Dated Dec. 1, 2022 From the International Searching Authority Re. Application No. PCT/IL2022/050756. (15 Pages).
Official Action Dated Mar. 14, 2024 from the US Patent and Trademark Office Re. U.S. Appl. No. 17/526,060. (30 pages).
English Summary Dated Aug. 5, 2024 of Notification of Office Action Dated Jul. 16, 2024 From the State Intellectual Property Office of the People's Republic of China Re. Application No. 202080086796.0. (2 Pages).
Summary Dated Oct. 30, 2024 of Notification of Office Action Dated Oct. 8, 2024 From the State Intellectual Property Office of the People's Republic of China Re. Application No. 202080094557.X. (4 Pages).
Notification of Office Action and Search Report Dated Oct. 8, 2024 From the State Intellectual Property Office of the People's Republic of China Re. Application No. 202080094557.X and its Machine Translation. (15 Pages).
Notification of Office Action and Search Report Dated Nov. 7, 2024 From the National Intellectual Property Administration of the People's Republic of China Re. Application No. 202080092059.1 and ItsSummary Translation Into English. (4 Pages).
Notice of Reason(s) for Rejection Dated Mar. 25, 2025 From the Japan Patent Office Re. Application No. 2022-530811 and Its Translation Into English. (22 Pages).
Notification of Office Action and Search Report Dated Apr. 8, 2025 From the State Intellectual Property Office of the People's Republic of China Re. Application No. 202080094557.X and its Summary and Machine Translation of Office Action into English.. (18 Pages).

\* cited by examiner

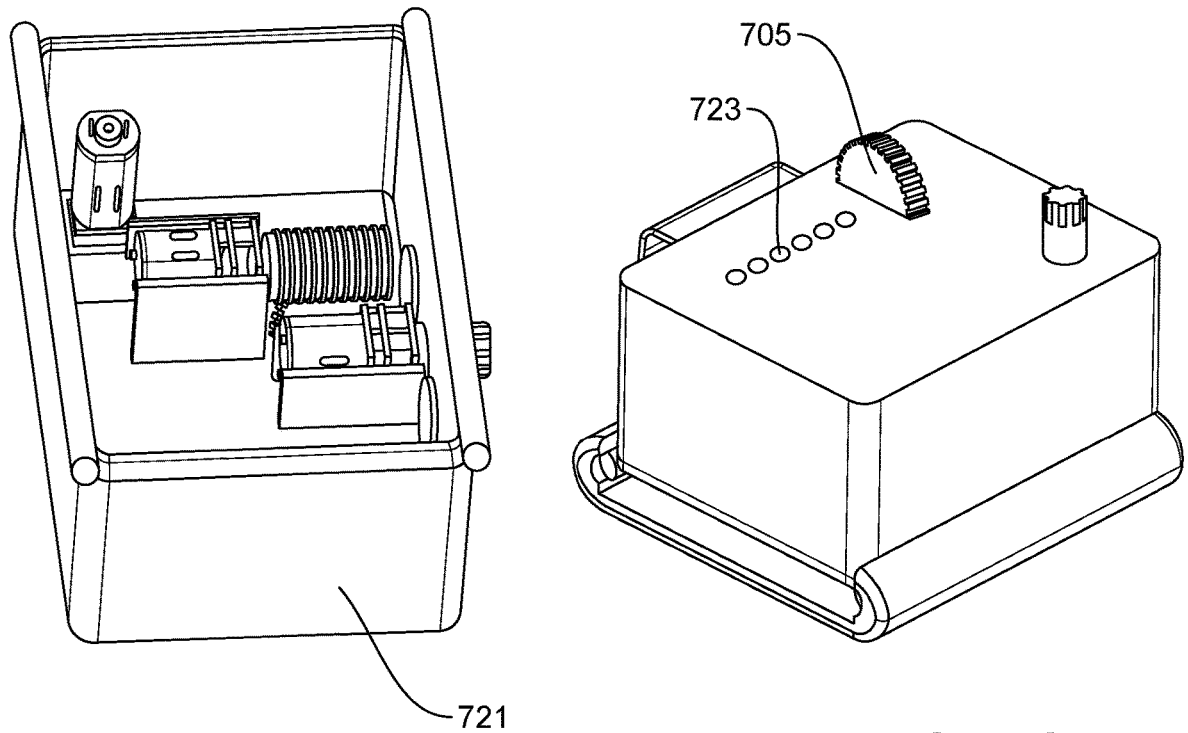
FIG. 7F
FIG. 7G
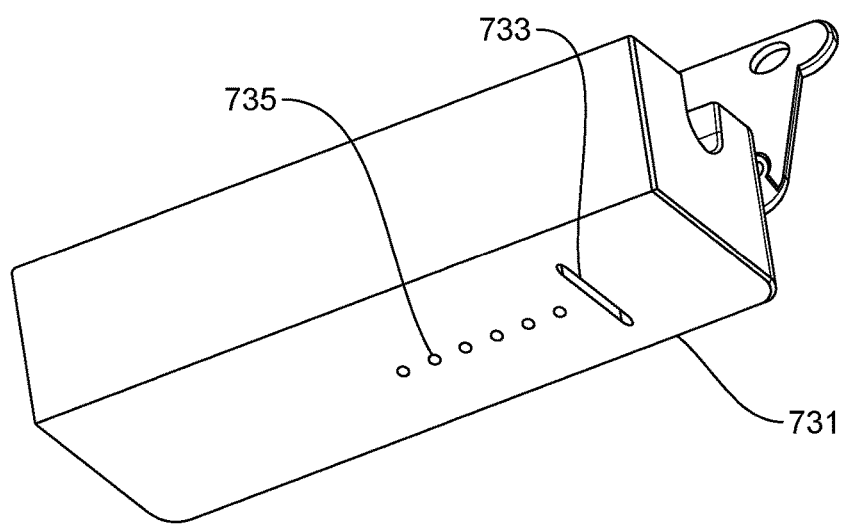
FIG. 7H

MODULAR ROBOTIC SYSTEM FOR DRIVING MOVEMENT OF SURGICAL TOOLS

RELATED APPLICATION(S)

This application is a National Phase of PCT Patent Application No. PCT/IL2020/051224 having International filing date of Nov. 26, 2020, which claims the benefit of priority under 35 USC § 119 (e) of U.S. Provisional Patent Application No. 62/941,842 filed on Nov. 28,2019, and of U.S. Provisional Patent Application No. 63/082,508 filed on Sep. 24, 2020. The contents of the above applications are all incorporated by reference as if fully set forth herein in their entirety.

PCT Patent Application No. PCT/IL2020/051224 is also related to co-filed, co-pending and co-assigned PCT application No. PCT/IL2020/051225 titled "ROBOTIC MANIPULATION OF A SURGICAL TOOL HANDLE" and PCT application No. PCT/IL2020/051226 titled "DEVICE FOR AUTOMATICALLY INSERTING AND MANIPULATING A MEDICAL TOOL INTO AND WITHIN A BODILY LUMEN" the contents of which are incorporated herein by reference in their entirety.

FIELD AND BACKGROUND OF THE INVENTION

The present invention, in some embodiments thereof, relates to a modular robotic surgical system and, more particularly, but not exclusively, to a system for manipulation of surgical tools received within separate tool receiving units.

U.S. Pat. No. 10,543,047 discloses "A robotic instrument driver for elongate members includes a first elongate member, and at least one manipulator mechanism configured to manipulate the first elongate member, and at least one articulating drive configured to articulate the first elongate member, positionable on a bed and beside a patient access site. The manipulator and articulating drive are positioned relative to each other a distance less than the insertable length of the first elongate member, stationary in position."

U.S. Pat. No. 10,524,867 discloses "An exemplary drive apparatus may include a roller assembly and a roller support. The roller assembly may have a first continuous surface, a second continuous surface, an open configuration for receiving an elongate member, and a closed configuration for securing the elongate member in the roller assembly. The roller assembly imparts axial motion to the elongate member along the first continuous surface, which maintains contact with the elongate member during the axial motion. The roller support rotates the roller assembly about the second continuous surface, which maintains contact with the roller support during rotational motion. The roller assembly and roller support to impart axial and rotational motion, respectively, independently of one another."

U.S. Pat. No. 8,480,618 discloses "A robotic catheter system is provided. The robotic catheter system includes a housing and a drive assembly coupled to the housing. The drive assembly is configured to impart movement to a catheter device. The catheter system includes a release structure permitting the drive assembly to be decoupled and removed from the housing without removing the catheter device from a patient."

SUMMARY OF THE INVENTION

According to an aspect of some embodiments there is provided a modular robotic surgical system comprising: a base; a plurality of tool-receivers arranged as separate units, each tool-receiver unit operable to move an elongate surgical tool received therein; a plurality of interface coupling pairs, each coupling pair comprising a first coupler as part of the base and a second coupler as part of each of the tool-receiver units; each of the tool-receiver units independently and interchangeably attachable to the base via the coupling pair.

In some embodiments, each of the tool-receiver units is configured to receive and drive movement of a single elongate surgical tool only.

In some embodiments, the tool-receiver units are shaped and sized to be mounted together onto the base.

In some embodiments, each of the tool-receiver units is configured to be attached to the base and aligned with respect to the base and/or with respect to at least one other tool-receiver unit via one or more of: magnetic attraction, an interference fit coupling, a fastener positioned externally to housings of the unit and the base respectively.

In some embodiments, the base comprises a housing including one or more motors.

In some embodiments, each of the tool-receiver units comprises a slot configured to receive the elongate surgical tool, and a plurality of tool moving elements located adjacent the slot.

In some embodiments, the slot is elongate and extends along a long axis of a housing of the unit.

In some embodiments, the tool moving elements comprise a set of wheels positioned diametrically opposing the slot, the wheels positioned and configured to contact an elongate surgical tool received within the slot and for moving the tool.

In some embodiments, the system comprises at least two tool-receiver units, and the at least two tool-receiver units are configured to be aligned parallel to each other such that an elongate surgical tool received within a first tool-receiver unit curves into a U-shape when exiting the first tool-receiver unit and before entering the second tool-receiver unit.

In some embodiments, the system comprises at least two tool-receiver units, and a single elongate surgical tool is moveable by the at least two tool-receiver units.

In some embodiments, the first coupler comprises a mechanical coupler extending from within a housing of the base, and the second coupler comprises a recess in a housing of each of the tool-receiver units into which the mechanical coupler extends, or vice versa.

In some embodiments, the mechanical coupler comprises a gear wheel, the gear wheel being positioned and configured to drive movement of tool-moving elements of each of the tool-receiver units in response to actuation of one or more motors of the base.

In some embodiments, the first coupler comprises a protrusion and the second coupler comprises a recess for receiving the protrusion, or vice versa.

In some embodiments, the first and second couplers comprise interfacing electrical connections.

In some embodiments, the system includes two or more coupling pairs which are symmetrically aligned to enable attachment of at least one tool-receiver unit and the base at a first orientation and a second orientation, and in the second orientation the tool-receiver unit is rotated 180 degrees relative to the first orientation.

In some embodiments, the elongate surgical tool is selected from the group of: a guidewire, a microcatheter, a guiding catheter, an intermediate catheter, a "rapid exchange" catheter.

In some embodiments, the system comprises at least one controller configured to coordinate actuation of tool-moving elements configured in each of the plurality of units.

In some embodiments, the tool moving elements drive one or both of: linear advancement and retraction of a tool received within the tool-receiver unit; rotation of a tool received within the tool-receiver unit.

In some embodiments, the system further comprises a remote control device, and the at least one controller is configured as part of the remote control device.

In some embodiments, the at least one controller is integrated in one or more of the tool-receiver units.

In some embodiments, each of the tool-receiver units comprises one or more sensors for indicating one or both of a presence of a tool within the tool-receiver unit, and a relative position of a tool received within the tool-receiver unit.

In some embodiments, the system comprises at least two tool-receiver units mounted onto the base, and in an assembled configuration the tool-receiver units do not protrude beyond an external perimeter defined by the base.

In some embodiments, a volume of the assembled system is less than 2500 cm$^\wedge$3 and a weight of the assembled system is lower than 800 grams.

In some embodiments, the system further includes a mounting on which the base is seated, and the base is slidable on the mounting.

In some embodiments, in an assembled configuration the system comprises only a single tool-receiver unit coupled to the base.

In some embodiments, in an assembled configuration the system comprises two or more tool-receiver units coupled to the base.

In some embodiments, the one or more motors are selected from the group of: a DC motor, an AC motor, a stepper motor, an electromagnetic actuator, a piezoelectric actuator, a pneumatic actuator, an hydraulic actuator, or any combination thereof.

According to an aspect of some embodiments there is provided a method of assembling and operating a modular robotic surgical system, comprising: selecting a system configuration according to a surgical procedure to take place; assembling the system by operably attaching at least one tool-receiver unit configured to receive an elongate surgical tool onto a base, the base comprising at least one motor configured to drive movement of the elongate surgical tool; positioning the assembled system with respect to a patient; and carrying out the surgical procedure by controlling movement of the elongate surgical tool within the body of the patient, the controlling comprising activating the at least one motor of the base.

In some embodiments, operably attaching comprises operably attaching at least two tool-receiver units onto the base, each tool-receiver unit configured to receive only a single elongated surgical tool, thereby carrying out the surgical procedure by controlling movement of at least two elongated surgical tools.

In some embodiments, controlling movement comprises controlling at least one of: linear movement of the elongated surgical tool, rotational movement of the elongated surgical tool, and actuation of a distal tip of the elongated surgical tool.

In some embodiments, controlling is performed using a remote control device which is in wireless communication with the system.

In some embodiments, the method further comprises disposing the system including the tool-receiver units and the base at the end of the surgical procedure.

In some embodiments, the method comprises adjusting the system configuration during the surgical procedure by removing or replacing the at least one tool receiver unit.

In some embodiments, the elongate surgical tool is selected from the group of: a guidewire, a microcatheter, an intermediate catheter, a guiding catheter.

In some embodiments, controlling comprises automatically limiting movement or generating movement of at least one elongated surgical tool according to movement of at least one other elongated surgical tool.

In some embodiments, at least one tool-receiver unit is provided pre-mounted onto the base.

In some embodiments, operably attaching comprises attaching the at least one tool-receiver unit at a selected orientation relative to the base.

In some embodiments, the method comprises selecting between two orientations between which the tool-receiver unit is rotated 180 degrees relative to the base.

In some embodiments, operably attaching includes directly attaching the at least one tool-receiver unit and the base without draping either one of the base or the at least one tool-receiver unit.

According to an aspect of some embodiments there is provided a tool-receiver unit for use with a motor base, the tool-receiver unit comprising: a first recess shaped and sized to receive a segment of an elongate surgical tool; one or more tool moving elements aligned adjacent the first recess, the one or more tool moving elements being configured to engage the elongate surgical tool for moving the tool, the tool moving elements being operably coupleable to the motor base.

In some embodiments, the tool-receiver unit comprises a housing accommodating the tool moving elements, the housing defining a second recess shaped and sized to receive a mechanical coupler of the base.

In some embodiments, the tool-receiver unit comprises a housing accommodating the tool moving elements, the housing further comprising a mechanical coupler protruding from the housing to be received within the base.

In some embodiments, the tool-receiver unit comprises a housing including a moveable cover portion which overlies the first recess.

In some embodiments, the elongate surgical tool is selected from the group of: a guidewire, a microcatheter, an intermediate catheter, a guiding catheter.

In some embodiments, the tool moving elements comprise wheels configured for at least one of: advancing and retracting the elongate surgical tool, rotating the elongate surgical tool.

In some embodiments, the first recess is elongate and is defined along an elongate shaft, and the tool-receiver unit is in operable communication with a motor which drives rotation of the shaft.

In some embodiments, the motor is configured within the base, and the tool—receiver unit comprises a slip ring which electrically couples the tool—receiver unit and the base regardless of a rotational position of the shaft.

According to an aspect of some embodiments there is provided a modular robotic surgical system for use with a "rapid exchange" catheter, comprising: a base comprising a housing including one or more motors; a guidewire-receiving unit configured to operably attach to the base such that movement of a guidewire received within the guidewire-receiving unit is controlled and driven by the one or more motors of the base; a rapid exchange catheter-receiving unit configured to operably attach to the base such that movement of a rapid exchange catheter received within the catheter-receiving unit is controlled and driven by the motors of the base; and a Y-shaped junction shaped and sized to enable insertion of the guidewire into a lumen of the rapid exchange catheter.

In some embodiments, the guidewire-receiving unit and the rapid exchange catheter-receiving unit are independently engaged with the base.

According to an aspect of some embodiments there is provided a modular robotic surgical system kit comprising: a system for example as described hereinabove; and a plurality of elongated surgical tools for insertion into the plurality of tool-receiver units, the elongated surgical tools selected from the group of: a guide wire, a microcatheter, a guiding catheter, an intermediate catheter.

According to an aspect of some embodiments there is provided a modular robotic surgical system comprising: a base; a plurality of tool-receiver units arranged as separate units, each tool-receiver unit operable to move an elongate intravascular tool received therein; each of the tool-receiver units operably attachable to the base and/or to at least one other tool-receiver unit; at least two of the tool-receiver units arranged to hold tools received therein in a parallel orientation to each other.

In some embodiments, each of the tool-receiver units comprises an elongate box-shaped housing.

In some embodiments, the plurality of tool-receiver units include at least two tool-receiver units which are aligned to hold tools received therein along a similar long axis.

According to an aspect of some embodiments there is provided a modular robotic surgical system comprising: a base; a plurality of tool-receiver units arranged as separate units, each unit operable to move an elongate surgical tool received therein; each of the units independently and interchangeably attachable to the base via an interface which transfers one or more of: mechanical driving force for driving movement of the tool; electrical power supply to one or more components of the unit which drive movement of the tool; and data for controlling movement of the tool by the unit.

According to an aspect of some embodiments there is provided a modular robotic surgical system comprising: a base comprising a housing including one or more motors; a plurality of tool-receiving units, each tool-receiving unit comprising a housing accommodating: one or more tool-moving elements; and a designated recess in which a tool or a segment of a tool is received, the recess being located adjacent the one or more tool-moving elements; each tool-receiving unit configured to independently operably attach to the base to actuate, via the one or more motors of the base, the tool-moving elements to move a tool received within the recess of the tool-receiving unit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4A:
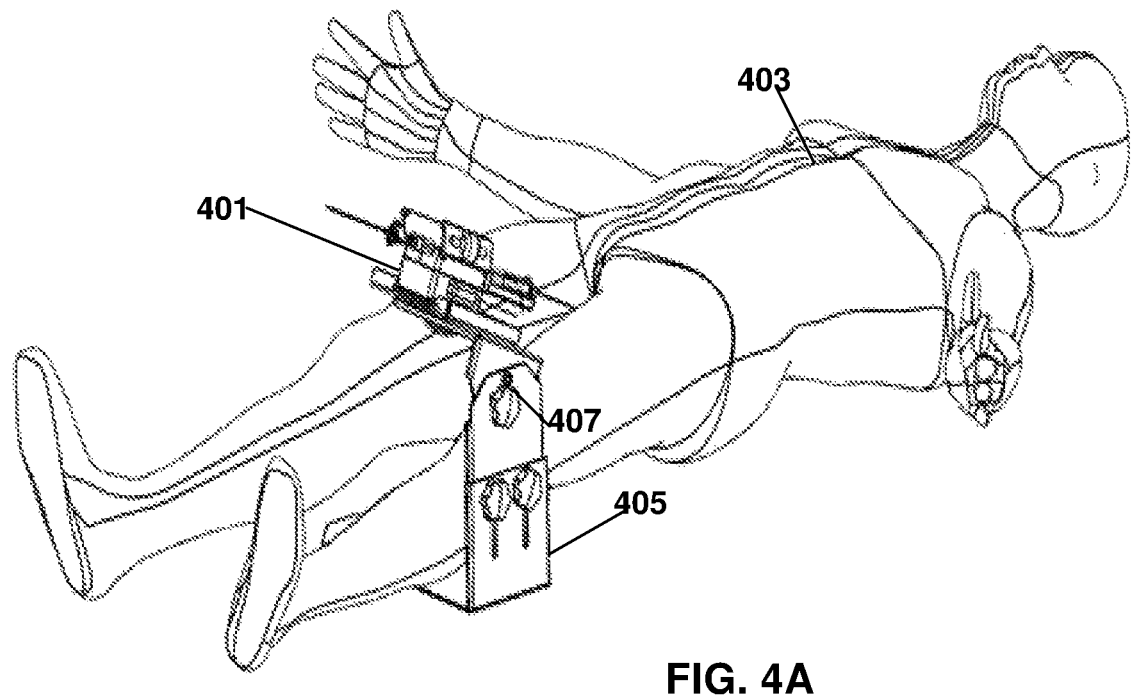
Figure 4B:
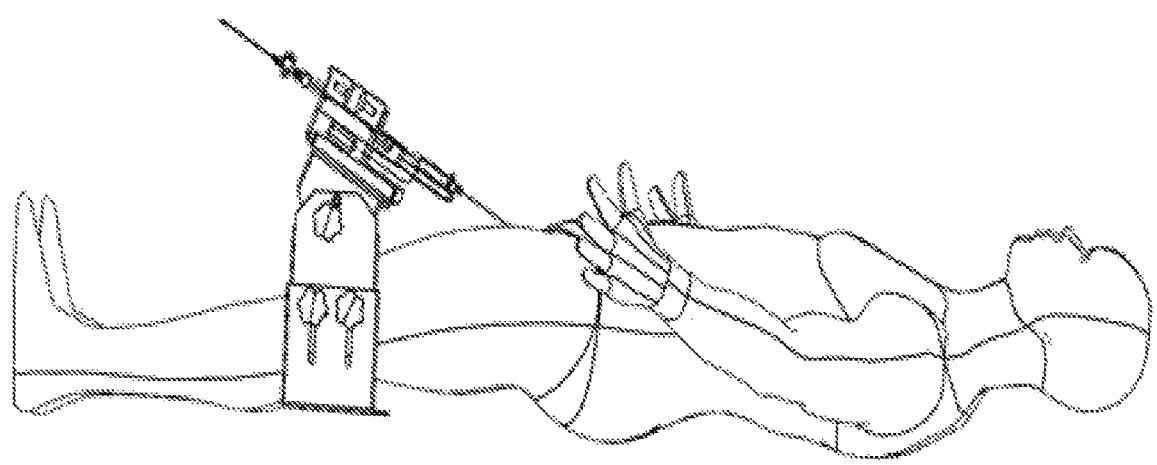
Figure 5A:
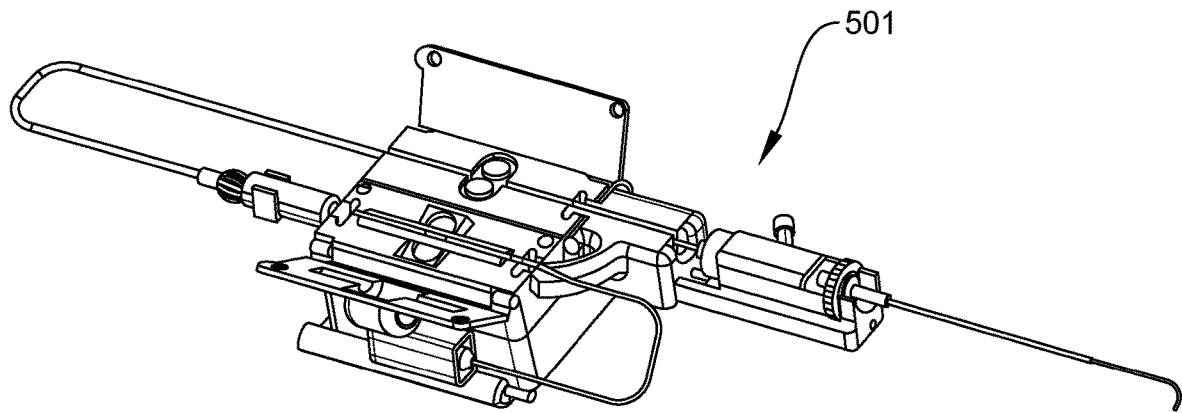
Figure 5B:
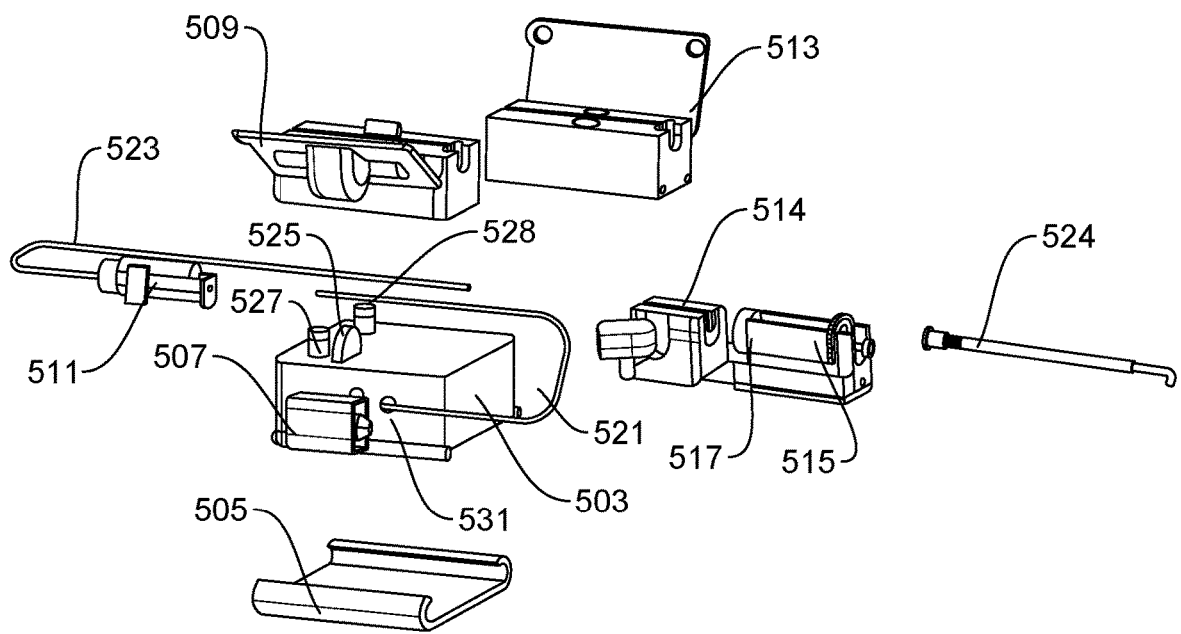
Figure 6A:
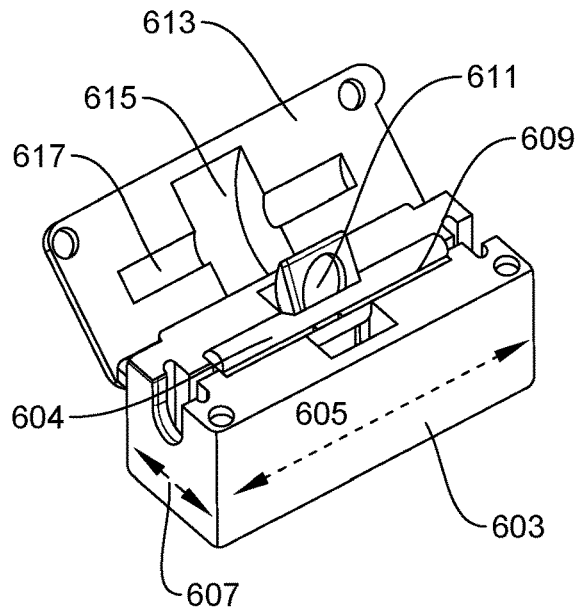
Figure 6B:
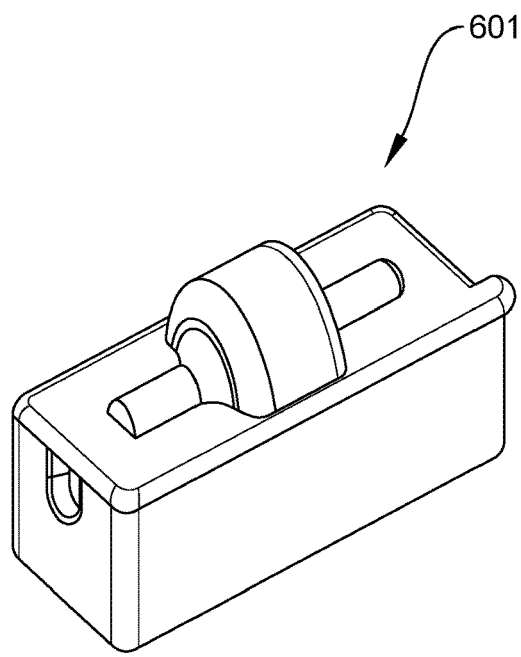
Figure 6C:
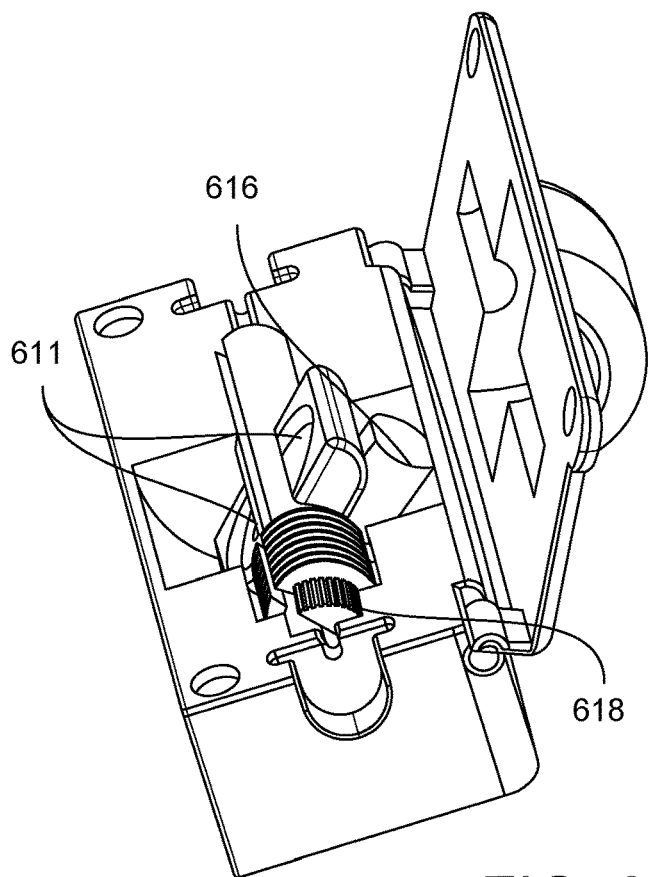
Figure 6D:
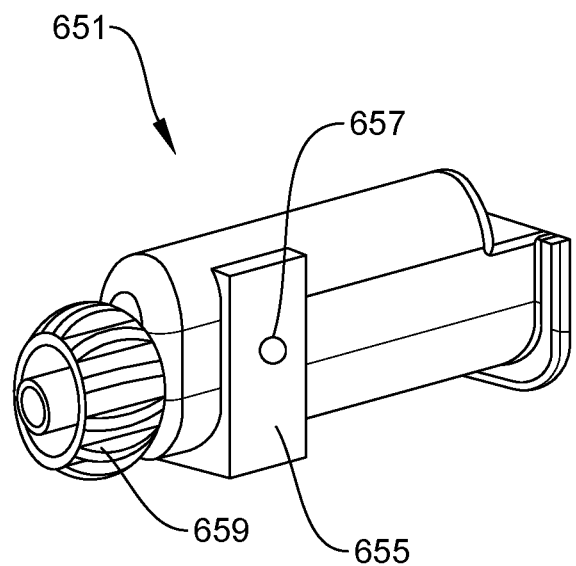
Figure 6E:
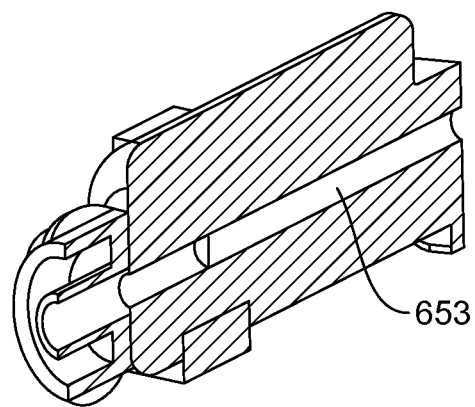
Figure 9A:
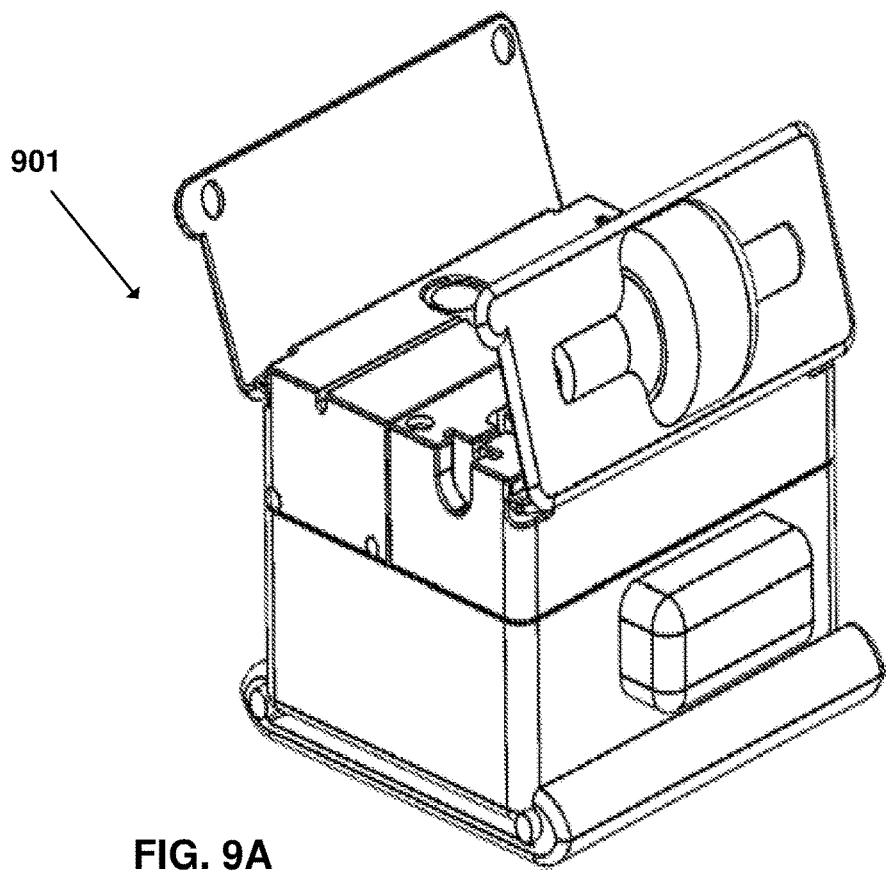
Figure 9B:
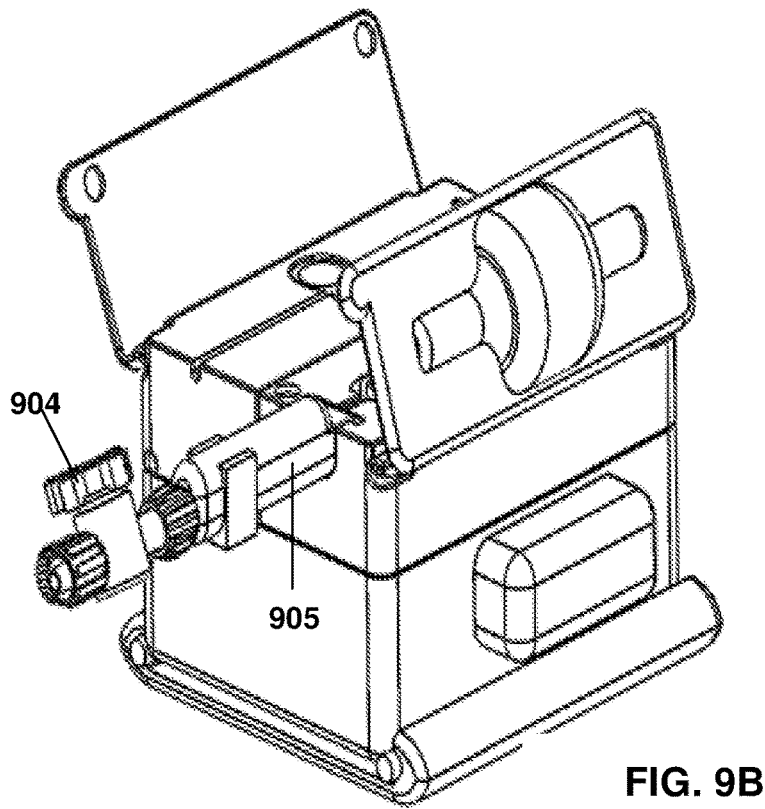
Figure 10A:
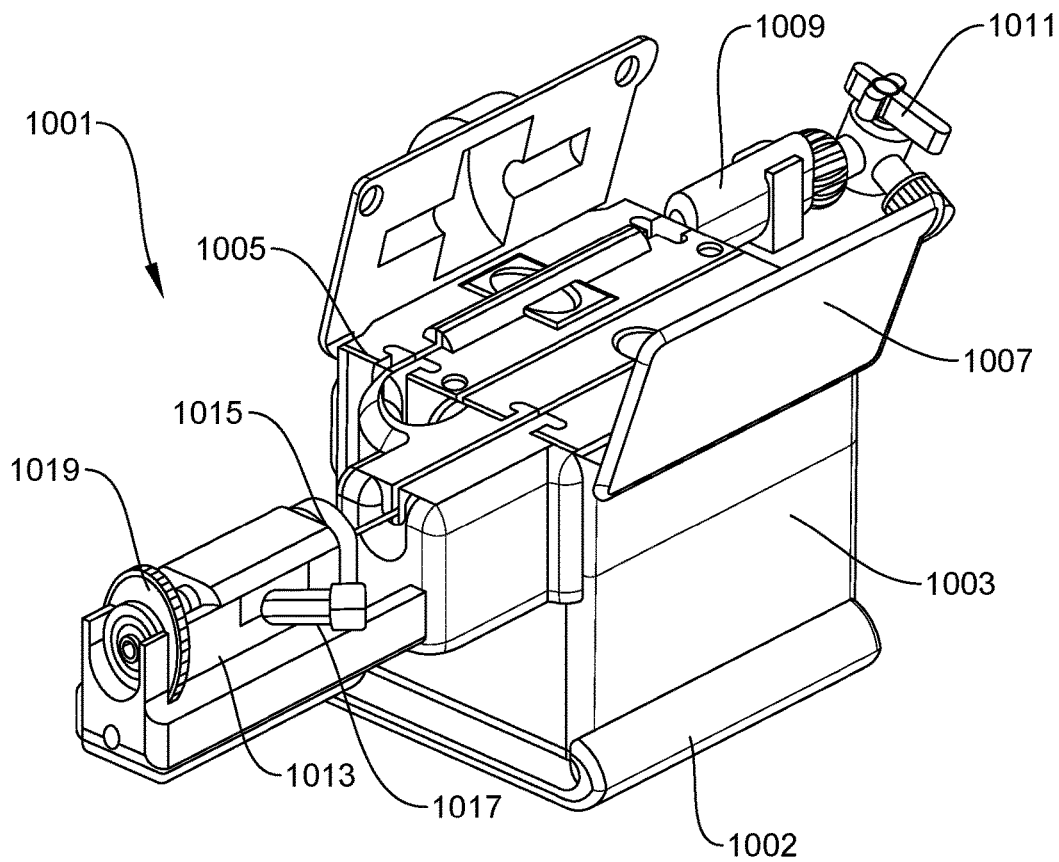
Figure 10B:
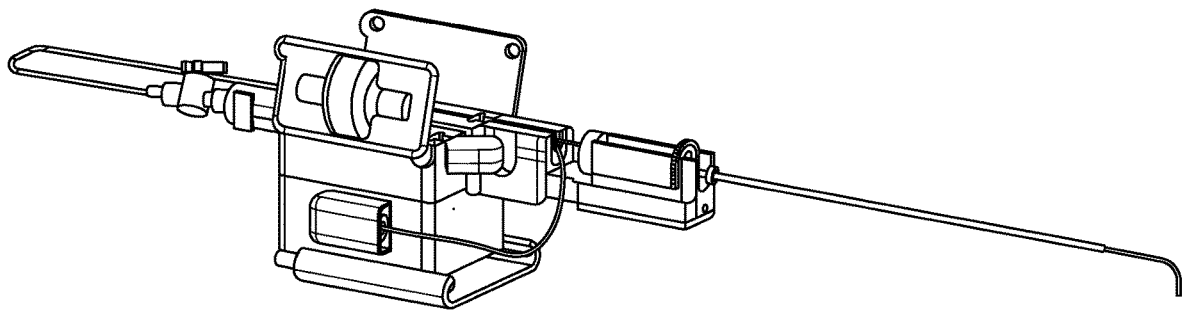
Figure 11A:
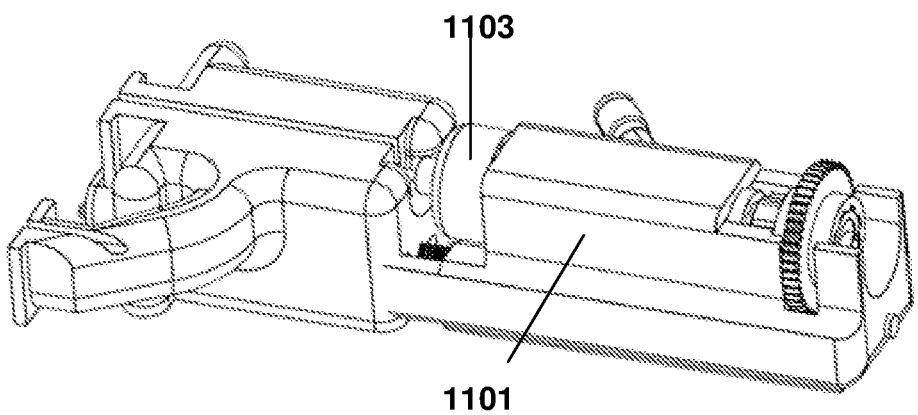
Figure 11B:
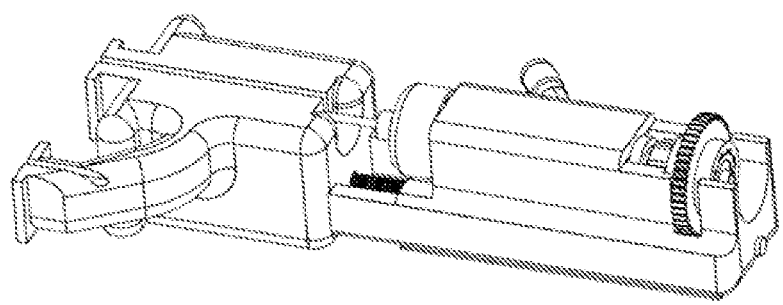
Figure 11C:
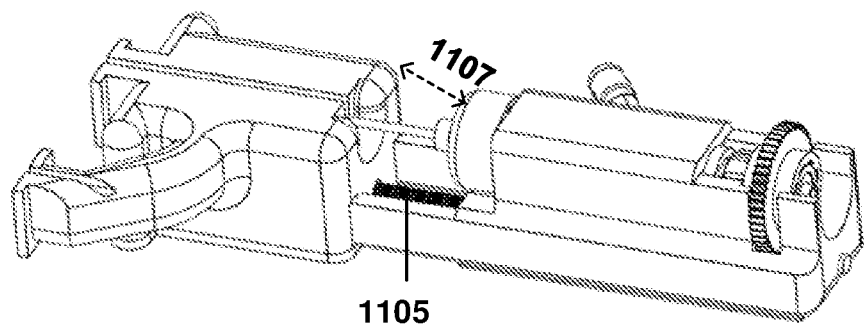
Figure 13A:
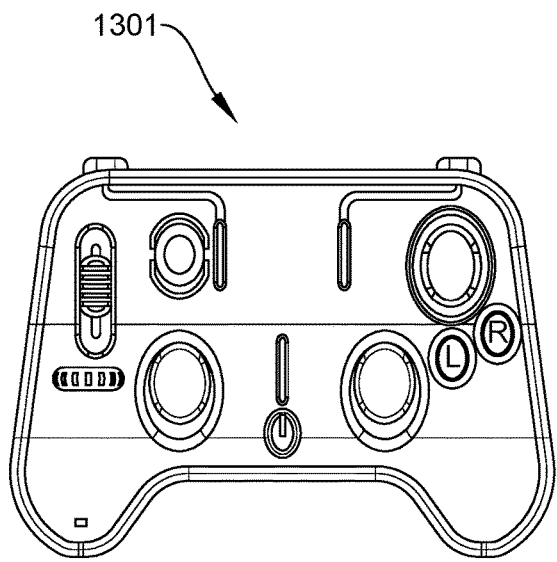
Figure 13B:
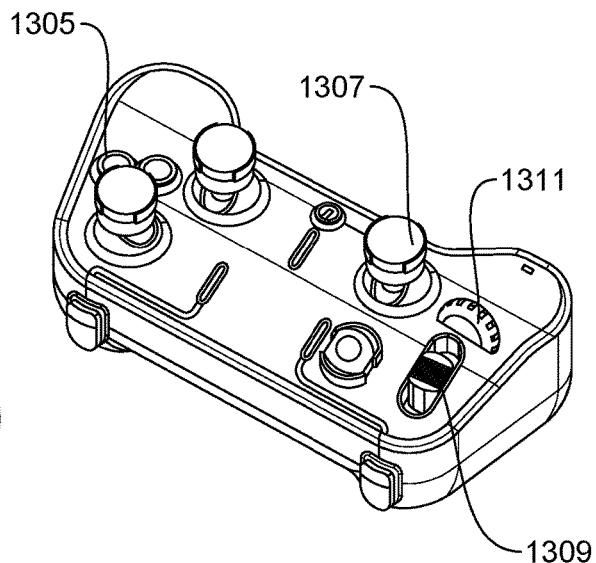
Figure 13C:
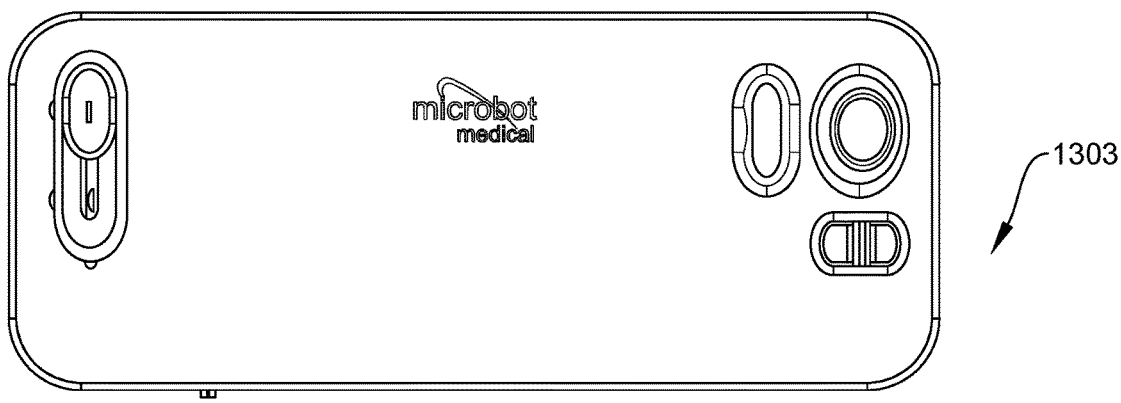
Figure 13D:
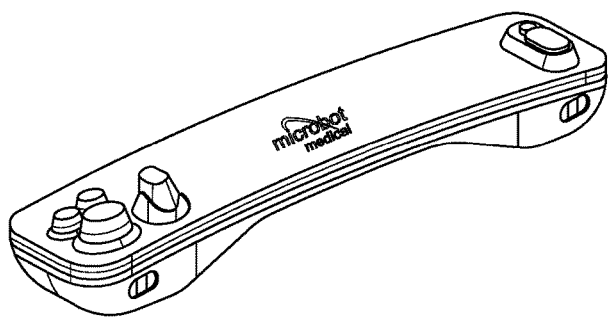
Figure 14A:
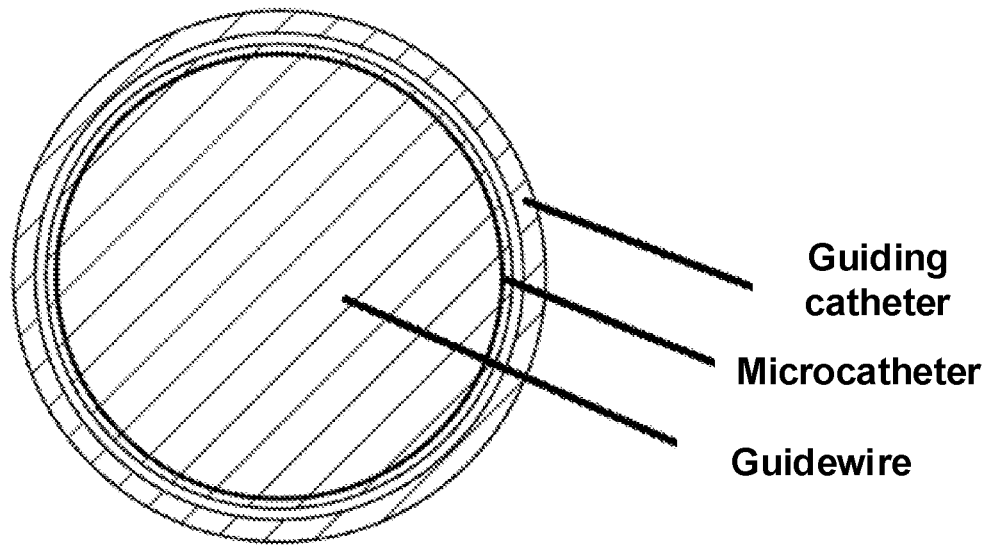
Figure 14B:
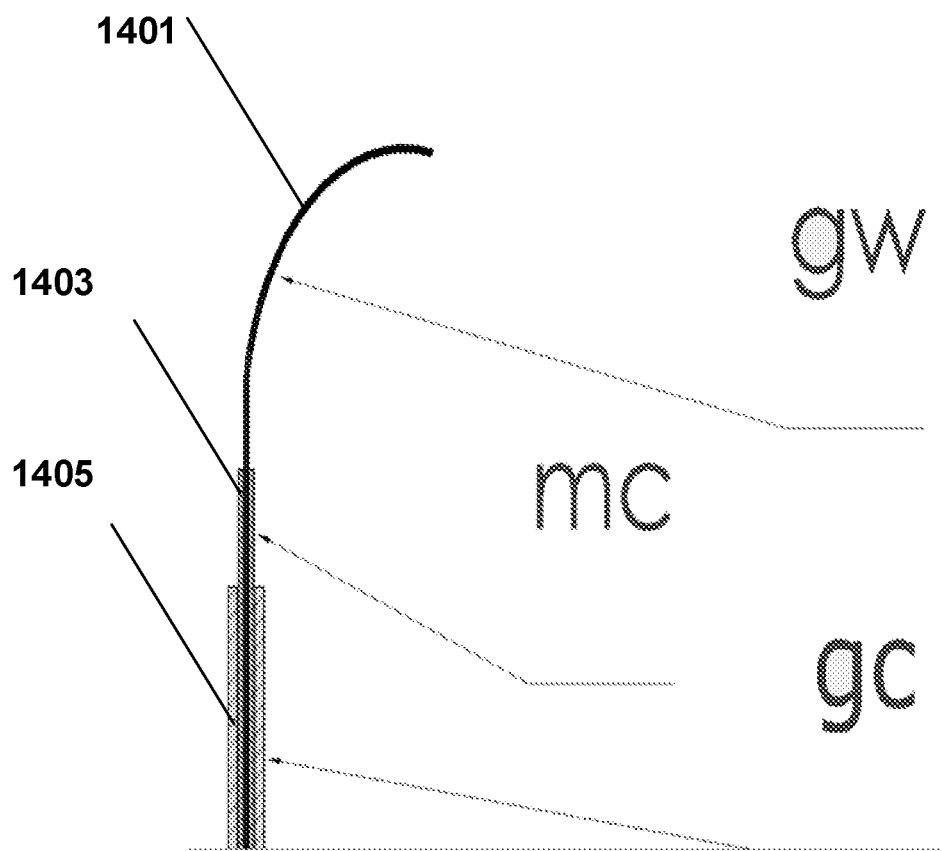
Figure 15A:
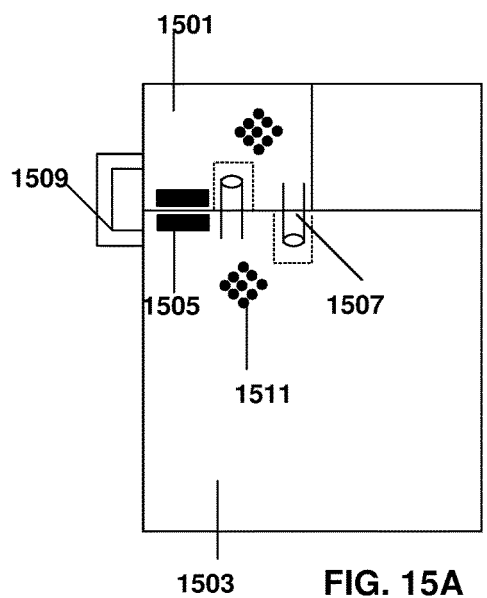
Figure 15B:
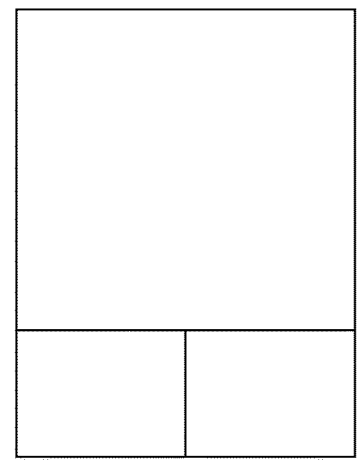
Figure 15C:
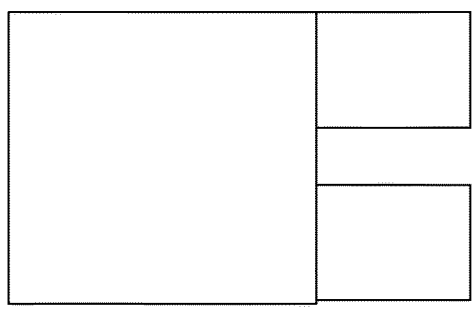
Figure 15D:
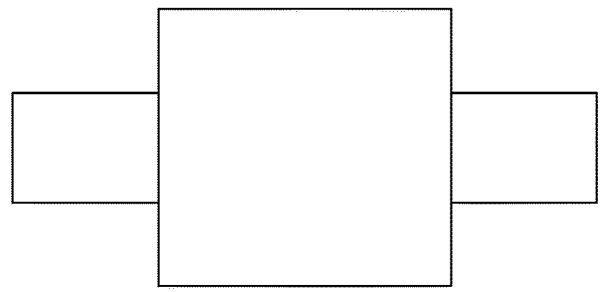
Figure 16A:
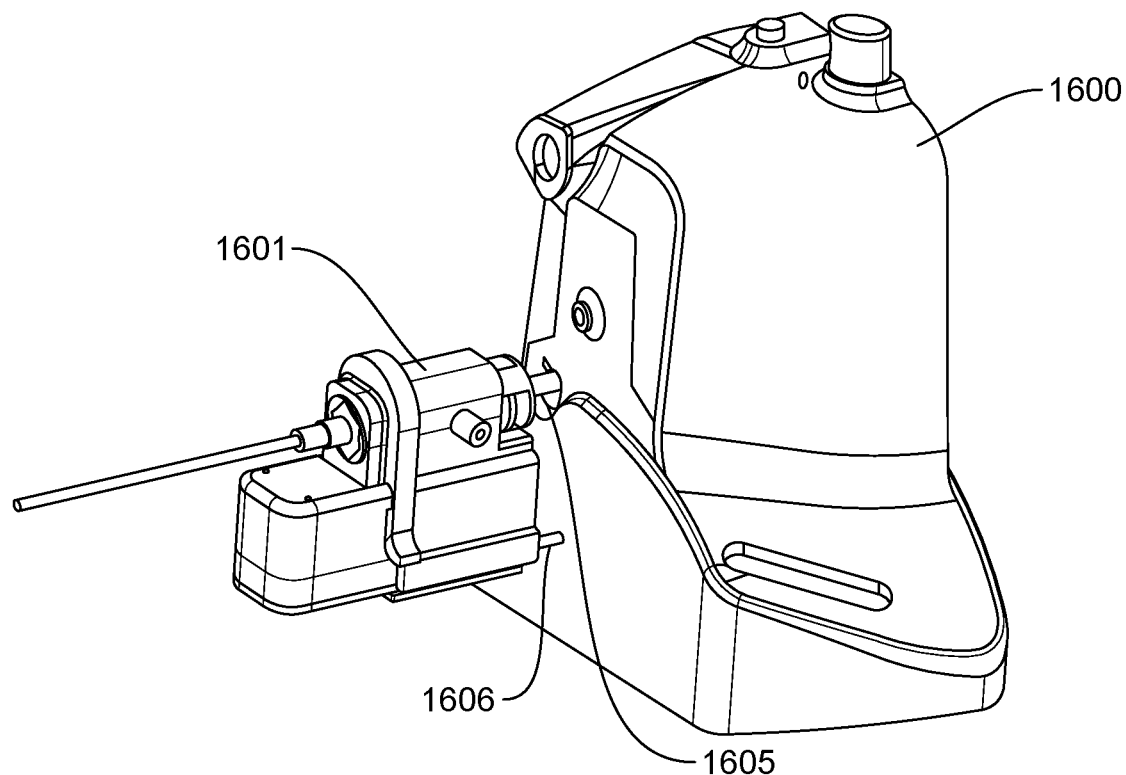
Figure 16B:
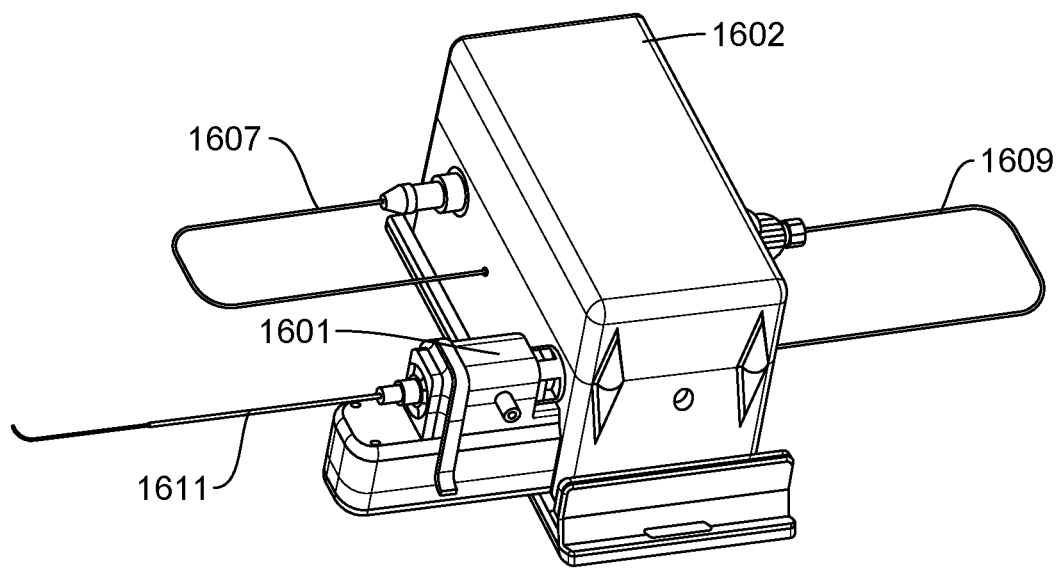
Figure 17A:
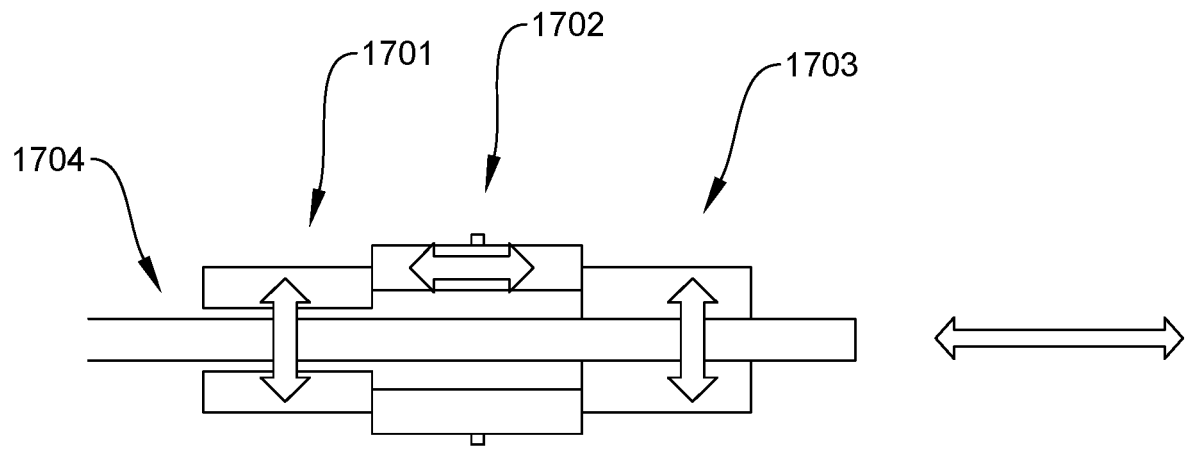
Figure 17B:
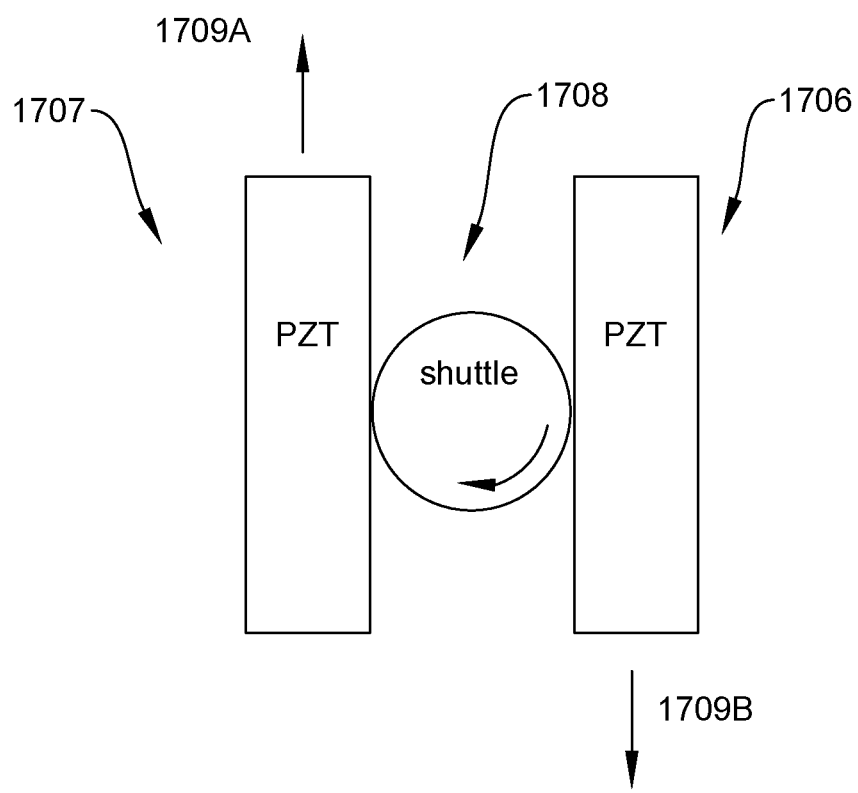
Figure 18:
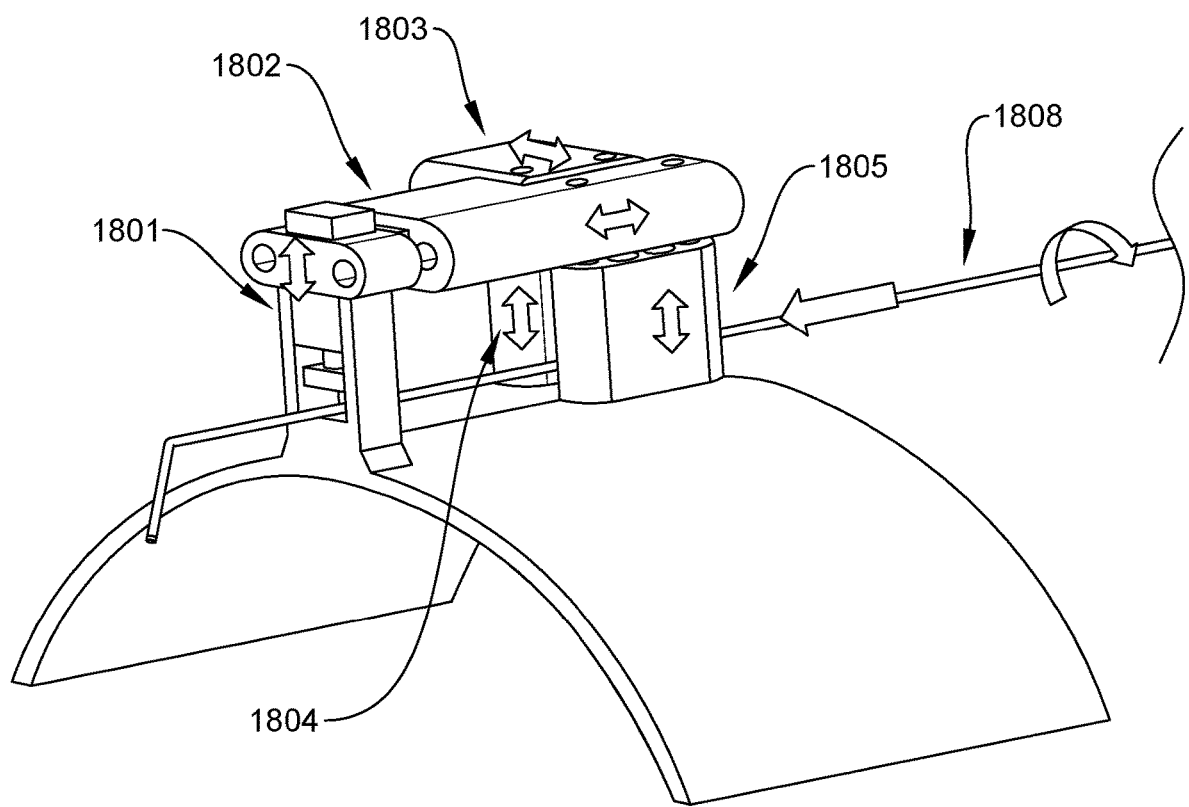

FIGS. 4A-B are an isometric view and a side view of a modular robotic surgical system positioned with respect to a patient, according to some embodiments;

FIGS. 5A-B are a side view (FIG. 5A) and an exploded view (FIG. 5B) of a modular robotic surgical system including a guide wire unit, a microcatheter unit, and a guiding catheter unit, according to some embodiments;

FIGS. 6A-C show a guidewire receiving unit (with an open cover (FIG. 6A, 6C) and a closed cover (FIG. 6B), according to some embodiments;

FIGS. 6D-E show a guidewire holder (shown at an isometric view (FIG. 6D) and a cross section view (FIG. 6E), according to some embodiments;

FIGS. 7A-E are various views of a base of a modular robotic surgical system, according to some embodiments;

FIGS. 7F-G are various views of another base configuration of a modular robotic surgical system, according to some embodiments;

FIG. 7H shows an example of a tool receiving unit configured to engage a base, according to some embodiments;

FIGS. 8A-D show attachment of a guidewire unit onto a base seated on a mounting (FIGS. 8A-B) and attachment of a microcatheter unit onto a base seated on a mounting (FIGS. 8C-D), according to some embodiments;

FIGS. 9A-B are isometric views of an assembled modular robotic surgical system, shown at FIG. 9A without a guidewire holder and at FIG. 9B with a guidewire holder protruding from an exit end of the guidewire receiving unit, according to some embodiments;

FIGS. 10A-B are isometric views of an assembled modular robotic surgical system, shown without inserted tools (FIG. 10A) and with inserted tools (FIG. 10B), according to some embodiments;

FIGS. 11A-C show a guiding catheter unit including a mechanism for linear movement of the guiding catheter, according to some embodiments;

FIGS. 12A-D are several views of a modular robotic surgical system configured for use a "rapid exchange" catheter, according to some embodiments;

FIGS. 13A-D are examples of a remote control device for controlling a modular robotic surgical system, according to some embodiments; and FIGS. 14A-B schematically illustrate an assembly of a guidewire, microcatheter, and guiding catheter, according to some embodiments;

FIGS. 15A-D schematically illustrate various arrangements of a base and tool receiving units, according to some embodiments;

FIGS. 16A-B show a slidable attachment of a guiding catheter unit, according to some embodiments;

FIGS. 17A-B schematically illustrate a piezoelectric actuated mechanism for linear translation and/or rotation of a surgical tool, according to some embodiments;

FIG. 18 is a schematic illustration of a device capable of imparting both linear and rotational motion on a surgical tool, according to some embodiments.

DESCRIPTION OF SPECIFIC EMBODIMENTS OF THE INVENTION

The present invention, in some embodiments thereof, relates to a modular robotic surgical system and, more particularly, but not exclusively, to a system for manipulation of elongate surgical tools received within separate tool receiving units.

A broad aspect of some embodiments relates to robotically manipulating elongate surgical tools using a system assembled and/or modified in accordance with the surgical procedure.

In some embodiments, the system configuration is selected for use based on the type of surgical procedure being performed. The system may be provided assembled and/or assembled on site by attaching only tool receiving units which are required for carrying out the procedure. Potential advantages of a system constructed according to the need may include simplified structure and operation, easy and fast setup, and a system of minimal size.

In some embodiments, the assembled system is compact and occupies a relatively small volume (e.g. a volume of less than 2000 cm$^\wedge$3, 2500 cm$^\wedge$3, 3500 cm$^\wedge$3, 5000 cm$^\wedge$3, 9000 cm$^\wedge$3 or intermediate, larger or smaller volume), enabling placing of the system in proximity to the patient (such as in proximity to the surgical entry point in the body). Alternatively, the system is mounted on the patient directly, e.g. assembled on the patient's leg or arm, in accordance with the surgical entry point. In some embodiments, the system is small enough so as not to interfere with other surgical room equipment, such as imaging modalities used during operation. Optionally, the system has only minimal or no floor footprint and/or ceiling footprint.

An aspect of some embodiments relates to a system comprising a base, and a plurality of tool receiving units, each unit independently attachable to the base. In some embodiments, the units are interchangeable. In some embodiments, each unit is configured for quick connection (and removal) to and from the base. Optionally, the system is assembled on site, for example right before surgery. In some embodiments, the system configuration may be adjusted, even during surgery, for example by attaching or removing one or more tool receiving units. Alternatively, the system is provided pre-assembled and ready to be used, optionally, even pre-loaded with the surgical tools.

In some embodiments, an interface between a tool receiving unit and the base transfers mechanical force for driving movement of a tool. For example, the base comprises one or more motors which drive movement of tool-moving elements (e.g. wheels) of the unit. Additionally or alternatively, the unit itself comprises one or more integrated motors.

In some embodiments, an interface between a tool receiving unit and the base electrically connects the unit and the base, such as for transferring power supply from the base to the unit.

In some embodiments, an interface between a tool receiving unit and the base transfers data, such as data related to control of tool movement. Optionally, at least a part of the data is received from a general system controller (optionally, from a remote control device).

In some embodiments, each unit is configured to receive an elongate surgical tool, e.g. an elongated intravascular surgical tool, for example: a guidewire, a microcatheter, a guiding catheter, an intermediate catheter. In some embodiments, the unit comprises tool moving elements which engage the tool upon insertion of the tool into the unit (such as into a designated recess in the unit housing), and are configured to move the tool, for example, linearly advance and/or retract the tool, rotate the tool, manipulate a distal end of the tool, and/or otherwise navigate or manipulate the tool. In some embodiments, the tool moving elements are actuated by the motor(s) of the base. In some embodiments, each unit drives movement of a single tool only. Optionally, a plurality of units drive movement of a same single tool.

In some embodiments, a tool receiving unit defines an interface for attaching with the base. In some embodiments, the base and unit are attached via an interface coupling pair, which includes a first coupler as part of the unit and a second coupler as part of the base. The first and second couplers may be configured for transferring mechanical force, conducting electricity, and/or transferring data. In some embodiments, the first and second couplers define a geometry at the interface between the unit and the base. For example, the first coupler is formed as a protrusion (optionally, an element extending from the base) and the second coupler is formed as a recess in the unit in which the protrusion is received. In some embodiments, the coupling pair defines a mechanical engagement with the motors of the base. For example, in some embodiments, motors (or portions thereof) and/or transmission elements (e.g. a gear wheel) protrude outwardly from the base and are received within a designated recess in the unit housing, where they are placed in operable contact with the tool moving elements of the unit. In some embodiments, the interface includes elements for aligning the unit relative to the base. Alignment may be achieved, for example, by magnetic attraction, a mechanical keying pattern, electronic engagement, and/or other. In some embodiments, the unit is mechanically locked to the base, for example to prevent relative movement of the base and unit during use.

In some embodiments, the system configuration is modified, optionally during operation, for example by removal and/or replacement of one or more tool receiving units. In some embodiments, one or more tools are removed or replaced during operation. In some embodiments, in the event of malfunction of a unit, the specific unit can be removed (and optionally replaced) without requiring the removal or replacement of other system units.

In some embodiments, in the assembled system, the designated recess (e.g. a slot) in each unit in which the tool is received remains accessible to the user at all system configurations.

In some embodiments, the system is controlled remotely, for example via a remote control device. In some embodiments, actuation of tool movement in each of the units is coordinated and controlled by a system controller. In some embodiments, the controller is configured to receive indications from one or more sensors configured in the units and/or in the base, the indications pertaining to one or more of: the presence of a tool inside the unit, a relative position of the tool, a tool movement performed, motor actuation performed.

An aspect of some embodiments relates to a single use robotic surgical system. In some embodiments, the system as a whole (such as including the base and optionally a mounting of the base), is disposed following use. Optionally, none of the system components (i.e. the tool receiving units and the base) are reusable. In some embodiments, the system is provided in a sterilized package, optionally already assembled. In some embodiments, electrical, mechanical and electromechanical components of the system are provided sterile.

In some embodiments, during manufacturing, the system is pre-assembled to include a base and selected units, and is optionally constructed according to the surgical need. Additionally or alternatively, the system is assembled on site, such as by the physician/nurse.

Potential advantages of a single-use system may include reducing or preventing the need for cleaning and/or sterilizing components following use; reducing or preventing the need to cover the system with a sterile cover (optionally, there is no need to place a sterile drape over the system); reducing or preventing the risk of cross-contamination between patients; shortening preparation time, and simplifying follow-up cleaning.

In some embodiments, a motor of the system (such as a motor which drives linear movement of a tool, a motor which drives rotation movement of a tool) includes a DC motor, an AC motor, a stepper motor, an electromagnetic actuator, a piezoelectric actuator, a pneumatic actuator, an hydraulic actuator, or any combination thereof.

It is noted that any dimensions and sizes listed herein are provided only as examples and should not be construed as limiting.

It is noted that a surgical tool for example as described herein may include any elongated endoluminal tool for use in the human body, such as in vasculature, the urinary system, the lymphatic system, the respiratory system, the digestive system and so forth. The terms surgical tool, elongated tool, endoluminal tool are generic interchangeable terms to describe all the above tools. Examples of such tools include, among others, a guidewire, a microcatheter, a guiding catheter, an intermediate catheter, a rapid exchange catheter. In some embodiments, the tool is shaped and sized for insertion into a body lumen, including for example a blood vessel, a duct, a tract, and/or other lumen.

It is noted that the terms "unit, "tool-receiving unit", "tool receiver unit" used interchangeably throughout the application may refer to a structure and/or a mechanism configured for engaging, receiving, holding, attaching to and/or moving an elongate surgical tool. In some embodiments, a "unit" comprises a housing including one or more of: tool moving elements (e.g. wheels); movement actuators (e.g. motors, motor transmission); controlling components (e.g. a controller, microprocessor and the like); communication modules.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
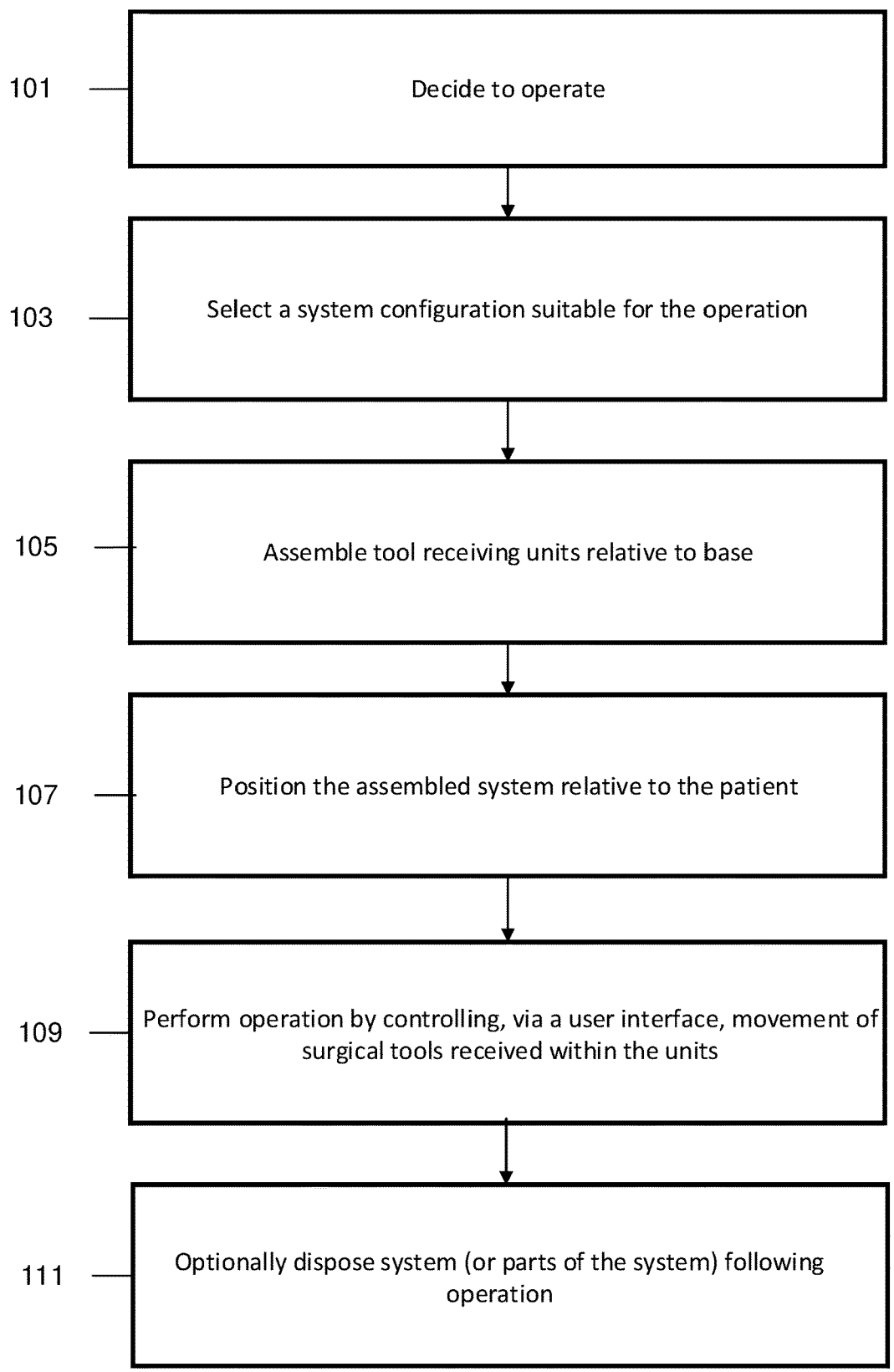
FIG. 1 is a flowchart of a general method of assembling and using a modular robotic surgical system, according to some embodiments.

Referring now to the drawings, FIG. 1 is a flowchart of a general method of assembling and using a modular robotic surgical system, according to some embodiments.

In some embodiments, a decision is made, for example by a physician, surgeon and/or other clinical personnel, to operate (101). In some embodiments, the operation is for therapeutic purposes. Additionally or alternatively, the operation is for diagnostic purposes.

In some embodiments, the operation involves catheterization. In some embodiments, the operation involves insertion of one or more tools into and/or through vasculature and/or into other non-vascular endoluminal structures. Examples of tools may include: a guide wire, a microcatheter, a rapid exchange catheter, a guiding catheter, a balloon catheter, a stent or coil, ablation tools, an intermediate catheter, a suction catheter, an ultrasound catheter, a pressure catheter and/or other tools. In some embodiments, the operation is a through-lumen based procedure. In some embodiments, the operation is an over-the-wire based procedure.

In some embodiments, a system configuration which is suitable for the specific operation is selected (103). The configuration may be selected by the physician and/or, in some embodiments, automatically recommended by the system, for example in response to inputting of the operation type and/or anatomical location being operated on and/or patient specific data.

In some embodiments, a system configuration defines which type and/or number of tool-receiving unit(s) will be used, depending on the type and/or number of tools required for the procedure. In some embodiments, a system configuration defines the relative alignment and/or position of the tool receiving units with respect to each other and/or with respect to the system motor base. In some embodiments, a system configuration is selected according to methods of operating of the tools received in the units (for example, a first tool being threaded into the lumen of another before advancement of the second tool).

In some embodiments, according to the configuration selected, one or more tool receiving units are assembled relative to the system base (105). In some embodiments, assembling is by mounting one or more tool receiving units onto a surface of the base housing. In some embodiments, assembling comprises arranging one or more tool receiving units laterally to the base and/or under the base and/or at any other position in which a tool receiving unit is operably coupled to the base. In some embodiments, assembling comprises aligning system components, for example aligning one or more units relative to the base and/or relative to each other. Alignment of components may be assisted by one or more of: visual markings, mechanical interfering elements (e.g. a protrusion and respective recess), magnetic attraction, snap fit mechanisms, sensors configured for indicating a position of the unit and/or base, sensors configured for indicating the type of unit being attached to the base (e.g. magnetic sensing, RFID, optical sensing, mechanical sensing, electrical sensing).

In some embodiments, the system is assembled by coupling one or more tool receiving units to the base by a mechanical coupling. Optionally, the mechanical coupling includes an element which extends from the housing of the base into the housing of a tool receiving unit, or vice versa. In an example, a gear wheel protrudes from the housing of the base to be received within a complementary recess formed in the housing of the tool receiving unit. In some embodiments, a mechanical coupling is configured to lock system components to each other, for example, lock a tool receiving unit to the base and/or lock tool receiving units to each other.

In some embodiments, the assembled system is substantially block shaped, for example having a square or rectangular compact configuration. Other configurations may include a cylindrical configuration, a rounded configuration. In some embodiments, the tool receiving unit and/or the base are provided with no housing. Optionally, mechanical coupling is provided by coupling at least one gear wheel between the base and the tool receiving unit. Optionally, electrical coupling is provided between the base and the tool receiving unit, e.g. via wiring.

In some embodiments, the assembled system is positioned relative to the patient (107). In some embodiments, the system is mounted onto the surgical bed, for example via a fixation. In some embodiments, the system is attached to the patient, for example mounted onto the patient's leg (e.g. to the thigh), to the patient's arm, and/or to other body parts. Attachment of the assembled system to the surgical bed and/or to the patient may be carried out using straps, bands, a rigid mounting, and/or other attachment means. In some embodiments, attachment to the bed is carried out using a stand which is stabilized relative to mattress and/or to the rail of the bed and/or to the floor. The modular system can then be mounted on the stand, for example attached via a snap fit mechanism, magnetic means, straps (e.g. Velcro), and/or other. In some embodiments, the stand is adjustable so as to enable use with patients of various sizes and/or different bed height and the like. In some embodiments, when setting a position of the system, one or more of a height, entry angle to the body, alignment of the system relative to the patient are selected. The system position may be defined with respect to the patient body or parts thereof (e.g. relative to the surgical entry point) and/or relative to the surgical bed and/or relative to other surgical room equipment, e.g. relative to imaging modules.

In some embodiments, loading of the tools onto the tool-receiving units (for example, each unit receiving a single tool) is performed on the assembled system. In some embodiments, loading of tools is performed after the system position is set; alternatively, loading of tools is performed before the system position is set. Optionally, a tool is preloaded onto a unit. In an example, a unit is provided in a sterilized package while already being loaded with a tool.

In some embodiments, operation is performed by controlling, via a user interface of the system, movement of the surgical tools received within the units (109). Exemplary manipulation of tools controlled by the system may include: linear advancement and/or retraction of a tool; rotation of a tool (e.g. about the tool axis); twisting of a tool; angular orientation of a tool (e.g. by curving a distal tip of a tool); articulation (e.g. of a distal tip of a tool); changing of mechanical properties of a tool, such as stiffness, for example by controlling, from a proximal end of the tool, a distal tip structure or inner arrangement.

In some embodiments, the user interface is configured on the modular system itself (e.g. as a screen and/or buttons and/or a joystick attached to the system units and/or to the base), and/or on a separate physician console, and/or on a separate remote control device. Control signals may be communicated via wired and/or wireless communication (e.g. network based communication) to the system.

In some embodiments, the modular system or specific components of it are disposed following operation (111). In an example, the tool-receiving units (along with the tools used) are disposed, and the system base is reusable. In another example, the system is disposed as a whole.

In some embodiments, the system is pre-packed in an assembled configuration.

Optionally, the assembled system is provided in a plurality of pre-assembled configurations suitable for a respective plurality of specific procedures. In use, a specific pre-packed and assembled configuration may be selected according to the operation to be performed.

Additionally or alternatively, the configuration is selected and implemented in the surgical room, by assembling selected system components (e.g. a base and selected tool-receiving units) together. In some embodiments, a system configuration is adjusted during operation according to the need. For example, a first stage of the procedure is carried out with the system assembled in a first configuration, and a second stage of the procedure is carried with the system assembled in a second configuration different than the first.

In some embodiments, specific tools and optionally their associated tool receiving units are removed or replaced during operation. In an example, in a "through lumen" type procedure, the microcatheter may remain in place while the guidewire can be removed or replaced by a therapeutic tool; in another example, in an "over the wire" procedure, the guidewire remains in place while the microcatheter is replaced with a therapeutic tool.

In some embodiments, for example when a procedure requires advancement through a catheter lumen, the guidewire is retracted from the catheter lumen manually and/or by the system (e.g. by operating a fast retraction button). In some embodiments, the guidewire is retracted and optionally replaced by a new guidewire; additionally or alternatively, the unit is replaced as a whole, inclusive of the guidewire.

In some embodiments, for example in an "over the wire" procedure, the microcatheter is retracted so that the guidewire extends distally to the microcatheter and is exposed and accessible. Optionally, the microcatheter is removed and optionally replaced.

Figure 2A:
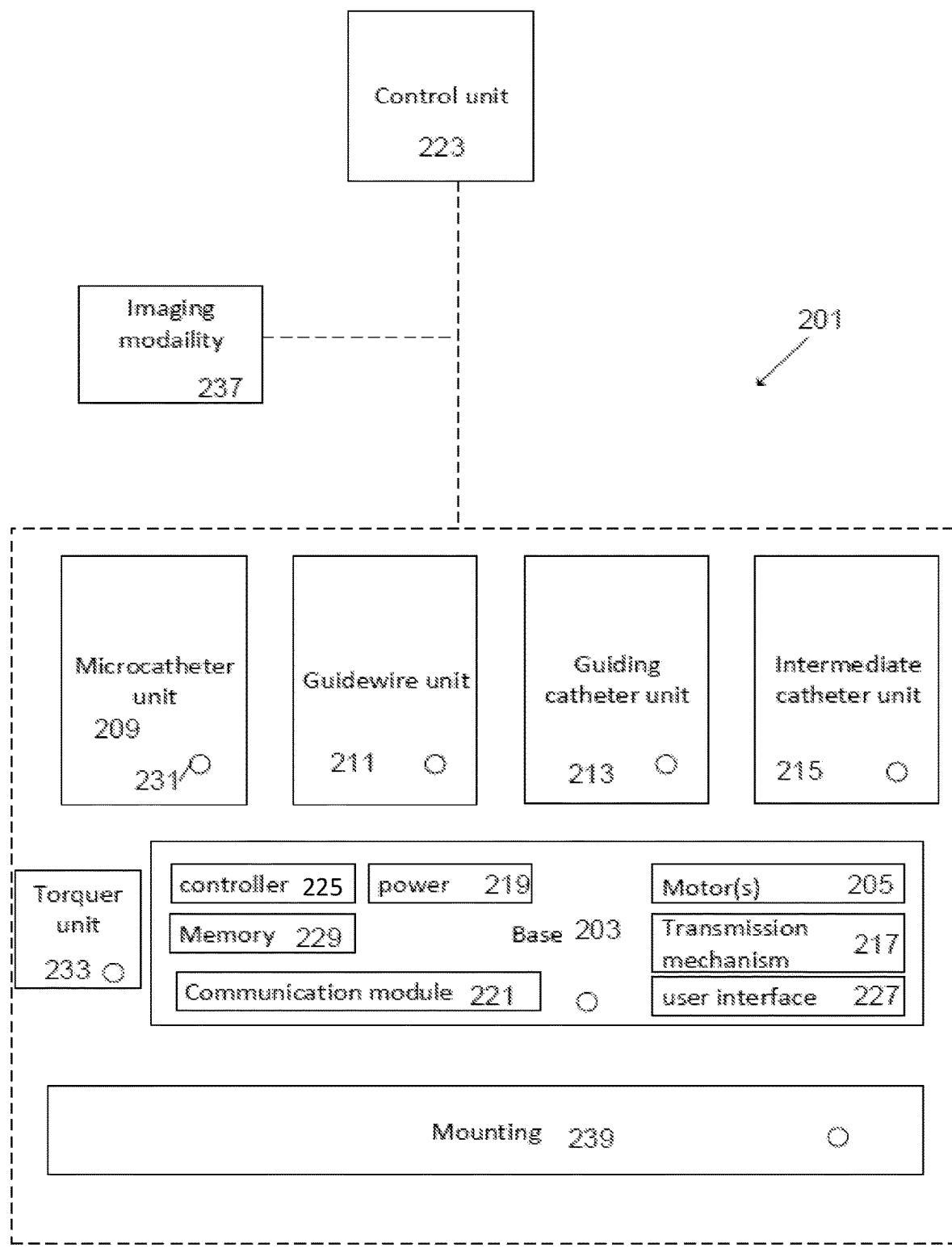
FIG. 2A is a schematic block diagram of a modular robotic surgical system, according to some embodiments.

FIG. 2A is a schematic block diagram of a modular robotic surgical system, according to some embodiments.

In some embodiments, a modular robotic system 201 is suitable for use in a surgical room. Optionally, one or more system components (such as controlling components, optionally imaging components) are physically separate from the rest of the system and may be used remotely.

In some embodiments, system 201 comprises a plurality (e.g. 1, 2, 3, 4, 5, 10, 20 or intermediate, larger or smaller number of tool receiving units. In some embodiments, each unit is configured to receive a tool and to move that tool. In some embodiments, each unit receives only a single tool. In some embodiments, movement of a single tool is actuated by a single unit. In some embodiments, movement of a single tool is actuated by more than one unit.

In some embodiments, one or more specific tool-receiving units are selected for carrying out an operation. Exemplary tool receiving units include: a microcatheter unit 209, a guidewire unit 211, a guiding catheter unit 213, an intermediate catheter unit 215.

Each of the units may be configured to drive linear movement (e.g. advancement and/or retraction) of the tool received therein, and/or drive rotational movement (e.g. axial rotation) of the tool received therein. In some embodiments, linear and rotational movements are actuated simultaneously in the same unit. In some embodiments, a unit may be limited to a single type of movement (e.g. drive linear movement only, drive rotational movement only).

In some embodiments, each unit is independently attachable to a base 203. In some embodiments, the base includes one or more actuators such as one or more motors 205, and optionally a transmission mechanism 217. In some embodiments, when a unit is operably attached to the base, motor(s) of the base drive movement elements (e.g. wheels, discs, rings) of a unit, which in turn move the tool received within the unit, for example, move the tool linearly and/or rotate the tool. Additionally or alternatively, a unit includes one or more integrated motors accommodated inside the unit housing.

In some embodiments, the one or more tools receiving units are configured to be mounted onto the base, and mechanically coupled to it. In some embodiments, a unit is mechanically coupled to and/or is in direct contact with one or more other units. Alignment and attachment of a unit to the base and/or to one or more other units may be carried out via one or more of: magnetic attraction, snap-fit interface, interference fit elements (e.g. a protrusion and respective recess), a connector (optionally a connector configured to provide a visual and/or audible indication upon attachment), and/or other coupling mechanisms. In some embodiments, once a unit is in place (e.g. relative to the base), the unit is locked in position to prevent its movement.

In some embodiments, the base comprises powering means 219, including for example a battery and/or connection means for mains electricity.

In some embodiments, the base comprises a communication module 221, for example for communicating with each of the tool-receiving units and/or with a general control unit 223 of the system.

In some embodiments, the base comprises an integrated controller 225. In some embodiments, controller 225 receives and/or sends operation signals to and/or from general control unit 223. General control unit 223 may be configured as a remote control device, a console, a control unit physically attached to the system base, or a combination thereof. In some embodiments, system controller(s) are configured to coordinate manipulation (e.g. linear movement, rotation) of tools received within the plurality of tool-receiving units.

Optionally, the base comprises a local user interface 227, for example configured as one or more buttons and/or a screen on the base housing.

Optionally, the base comprises a memory component 229. Memory 229 may store, for example: parameters related to tool movement, such as speed of movement, rotation, translation, angulation; indications obtained by one or more system sensors, such as a measure of force acting on the tool, stiffness of the tool; parameters related to the patient body and sensed by the inserted tools (e.g. heart rate, blood pressure, temperature, oxygenation level, and/or other sensed parameters).

In some embodiments, system components include sensors (schematically illustrated as circles 231). Sensors incorporated in a tool receiving unit may be used, for example, for detecting whether a tool has been inserted into a unit; a relative position of the tool; a position of the movement elements (e.g. of the wheels); actual movement of the movement elements (e.g. by a counter counting the number of wheel rotations); for communication with other system sensors, and/or for other measurements and/or indications. Sensors incorporated in the base may be used, for example, for detecting a motor position; detecting a motor rotation rate; detecting whether unit(s) have been attached onto the base; communicating with other system sensors. Sensors of various types may be used, such as optical sensors, pressure sensors, force measurement sensors, speed sensors, sensor for detecting electrical current, flow sensors, position sensors (e.g. optical, magnetic, electrical position sensors).

In some embodiments, system 201 includes a torquer unit 233, configured to affect rotational movement of a guidewire received within the guidewire unit. In some embodiments, torquer unit 233 actuates a distal tip of a guidewire, for example, controlling a curvature and/or orientation and/or stiffness of a distal tip of a guidewire. The torquer unit may actively control rotation of the guidewire and/or passively allow for rotation in response to rotation by the guidewire receiving unit. In some embodiments, the torquer unit is attached to the base.

In some embodiments, system 201 includes an integrated imaging modality 237.

Alternatively, the system is configured to be operably attached to (for example, communicate with) an existing imaging modality. An imaging modality may include, for example, X-ray fluoroscopy, CT, cone beam CT, CT fluoroscopy, MRI, ultrasound, or any other suitable imaging modality.

In some embodiments, system 201 comprises a mounting 239 for placing the system (or components of it) relative to the patient and/or relative to the surgical bed. In some embodiments, the mounting comprises or is configured to attach to an adjustable fixture. Optionally, a height and/or angle and/or distance of the system relative to the patient (e.g. relative to the location of body entry) and/or relative to the bed are adjustable.

The system may be provided in a ready-to-use assembled configuration, or alternatively assembled on site.

Some exemplary system configurations may include:
A configuration including a guidewire unit and a microcatheter unit;
A configuration including a guidewire unit, a microcatheter unit, and a guiding catheter unit;
A configuration including a microcatheter unit (optionally without a guidewire unit, when the microcatheter itself is a steerable/deflectable microcatheter);
A configuration including a guidewire unit, a microcatheter unit, and an intermediate catheter unit (for example, for use in vascular procedures). In an example, an intermediate catheter is used as an additional carrier to the microcatheter in neurovascular procedures.

In an exemplary system configuration, the guidewire unit is configured for rotating the guidewire (optionally about the guidewire axis), and for moving the guidewire linearly (advancing and retracting), and the microcatheter unit is configured only for moving the microcatheter (in which the guidewire is received) linearly (advancing and retracting). In some embodiments, the microcatheter unit also drives rotational movement of the microcatheter.

In an exemplary use, a guidewire receiving unit and a microcatheter receiving unit are used for a "through lumen" procedure such as an embolization procedure (using coils, glue, beads or other embolization tool), a procedure in which localized medication is delivered, an ablation procedure. In the example of an embolization procedure, the guidewire may be retracted and then an embolization tool may be administered through the lumen of the microcatheter. In another example, a stent retriever and/or aspiration tool is administered through the microcatheter lumen after retracting the guidewire.

In another exemplary use, ballooning and/or stenting procedures are performed using a guidewire receiving unit (holding a guidewire) and a designated unit for a balloon catheter or stent catheter (holding the balloon/stent catheter).

Figure 2B:
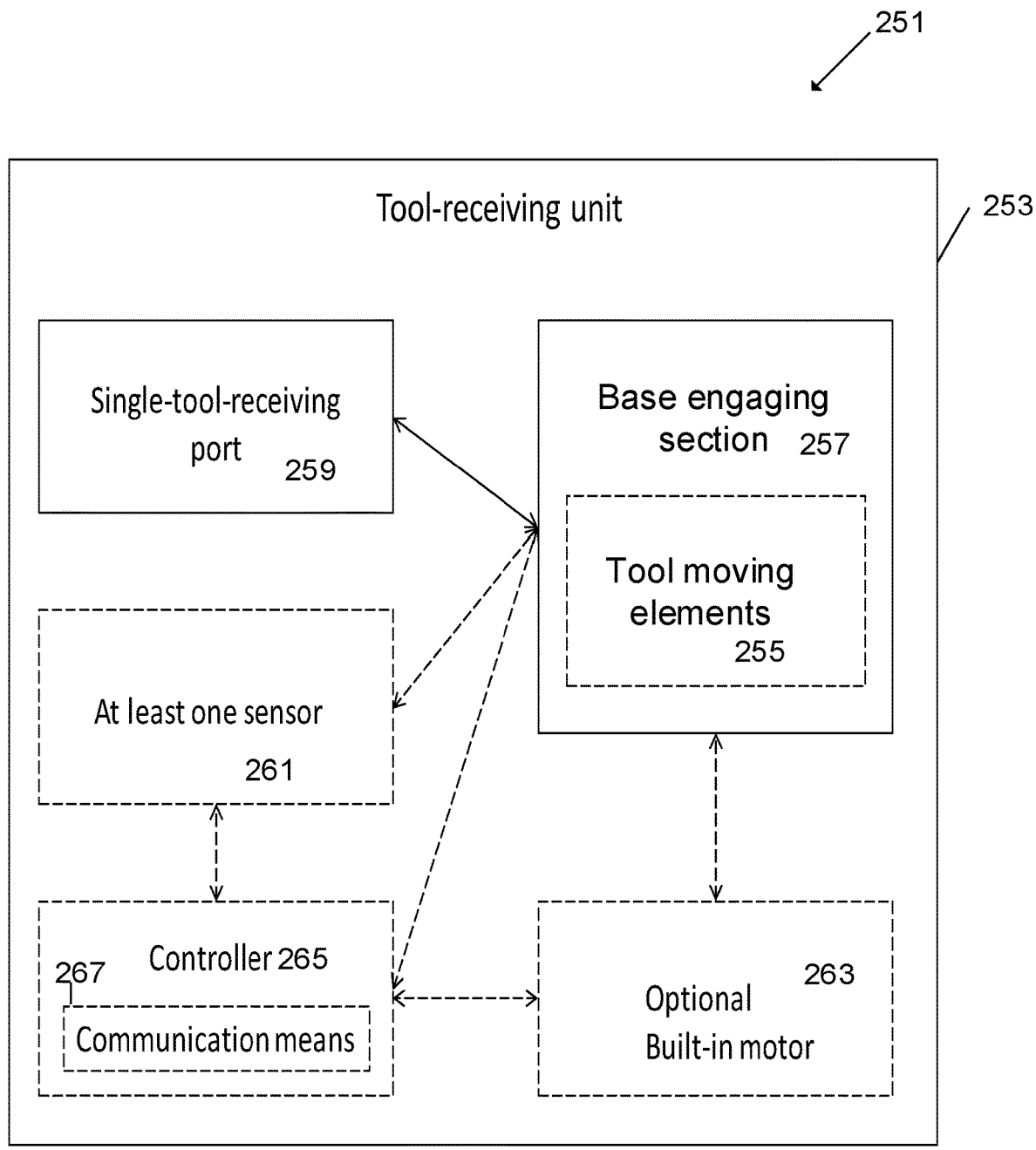
FIG. 2B is a schematic block diagram of a tool receiving unit, according to some embodiments.

FIG. 2B is a schematic block diagram of a tool receiving unit, according to some embodiments.

In some embodiments, a tool-receiving unit 251 is comprised of a housing 253 encasing components for example as described hereinbelow.

In some embodiments, the tool receiving unit comprises tool moving elements 255, for example, wheels, configured and positioned to engage a tool received within the unit.

In some embodiments, the tool receiving unit comprises a base engaging section 257. Optionally, the base engaging section comprises a recess in which a mechanical coupler protruding from the system base is received. Additionally or alternatively, the base engaging section comprises a mechanical coupler which protrudes from the unit housing 253 to operably engage the base. In some embodiments, the mechanical coupler is a gear, a wheel, a motor and/or other element shaped and configured to transfer force and/or drive movement of another component.

In some embodiments, a coupling between the unit and the base includes a magnetic coupling. In some embodiments, a coupling between the unit and the base includes an electrical coupling, for example allowing electrical power supply to the unit (e.g. to the tool moving elements of the unit and/or to other components driving movement of the tool moving elements, e.g. motors). An electrical coupling may include, for example, slip rings, electrical connectors, relay circuitry and/or other.

In some embodiments, the tool moving elements are driven by the motor(s) of the base to which the unit is attached. Additionally or alternatively, the unit comprises its own, integrated motor 263.

In some embodiments, the tool receiving unit comprises a tool receiving port 259. Optionally, the port is configured as an elongate slot, extending for example along a long axis defined by the unit housing. In some embodiments, the slot is straight, extending for example along a long axis of the unit housing. Alternatively, the slot defines a winding or curved path, which may increase a contact surface area between the tool and the tool moving elements (e.g. wheels), potentially improving traction.

In some embodiments, when the tool is inserted into the slot, the tool-moving elements engage the tool, for example, elements configured as wheels engage the tool, optionally on diametrically opposite positions. In some embodiments, the tool moving elements are spring actuated, so that upon insertion of a tool into the slot, the spring(s) press the elements against the tool.

In some embodiments, a tool receiving unit is configured to receive tools of various diameters. For example, a guidewire receiving unit may be configured to receive guidewires of diameters between, for example, 0.18-0.25 mm, 0.5-1.14 mm, 0.18-1.14 mm or intermediate, larger or smaller diameter. In some embodiments, the spring actuated positioning of the tool-moving elements enables the use of tools of various diameters.

In some embodiments, the tool receiving unit comprises at least one sensor 261. In an example, the sensor is configured to detect presence of a tool received within the unit. Optionally, the sensor is configured to detect presence of a tool within a second tool, e.g. presence of a guidewire within a microcatheter. Optionally, the sensor is configured to detect a relative position of a tool received within the unit (for example, detect a length of a tool elongate section which has been advanced and or retracted).

In some embodiments, optionally, the tool receiving unit comprises its own controller 265 and communication means 267. Additionally or alternatively, the tool receiving unit itself does not include computational elements, and its components are controlled directly by controller(s) of the base and/or by remote control device(s) and/or other interface.

Optionally, the tool receiving unit comprises its own power supply, for example, via a battery and/or connecting means to mains electricity.

Figure 3:
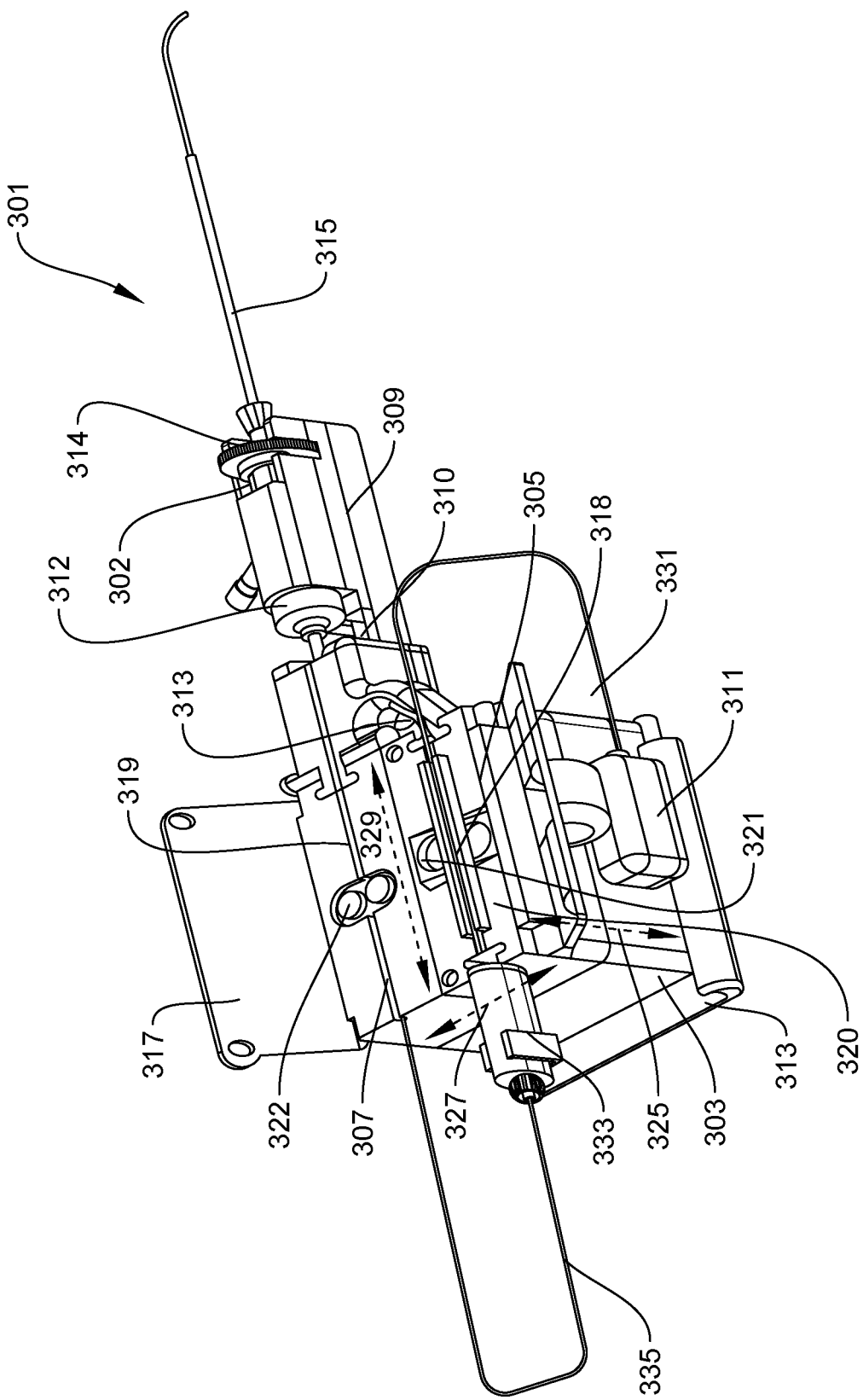
FIG. 3 illustrates an exemplary configuration of an assembled modular robotic surgical system, according to some embodiments.

FIG. 3 illustrates an exemplary configuration of an assembled modular robotic surgical system, according to some embodiments.

In the example shown, assembled system 301 comprises the following components: a base 303; a guidewire receiving unit 305; a microcatheter receiving unit 307; a guiding catheter receiving unit 309; a torquer unit 311; a mounting 313 on which base 303 can be moved (e.g. by sliding) linearly.

In some embodiments, the guidewire receiving unit 305 and the microcatheter receiving unit 307 are each configured to be separately mounted onto a housing of the base 303. In some embodiments, unit housings are aligned with respect to the housing of the base, for example so that the unit housing does not extend beyond the perimeter of the base. Optionally, when the units are fully aligned with the base and optionally locked to the base, a compact box shaped arrangement (e.g. having a rectangular or squared cross section profile) is formed. Alternatively, the assembled system comprises a round cross section profile.

In some embodiments, the assembled system is relatively small in size, for example having a height 325 less than 10 cm, 13 cm, 20 cm or intermediate, longer or shorter; a width 327 less than 7 cm, 12 cm, 15 cm or intermediate, longer or shorter; and a length 329 less than 15 cm, 17 cm, 20 cm or intermediate longer or shorter as measured without the guiding catheter unit or a length less than 18 cm, 25 cm, 30 cm or intermediate, longer or shorter as measured with the guiding catheter unit. In some embodiments, the assembled system is lightweight, for example weighing no more than 400 grams, 600 grams, 900 grams or intermediate, higher or lower weight. A potential advantage of a compact and lightweight system may include the ability to position the system at various positions with respect to the patient and/or with respect to the surgical bed, and even on the patient's body. Another potential advantage may include less interference with other surgical room equipment such as imaging modalities, for example as compared to larger, bulkier systems. Another potential advantage is that the system has no or minimal floor footprint, and potentially does not occupy floor space.

In some embodiments, as shown, one or more units are mounted on a top face of the base housing. Additionally or alternatively, units may be attached to one or more other faces of the base, for example, the base might be positioned on top of a unit, sideways adjacent a unit, or combinations thereof.

In some embodiments, torquer unit 311 is mounted on a face of the housing of the base which is different than the face on which units such as unit 305 and 307 are mounted. In some embodiment's, torquer unit affects movement of a distal tip of the guidewire. Alternatively, the torquer unit affects movement of the entire length of the guidewire.

In some embodiments, guiding catheter receiving unit 309 extends distally from microcatheter receiving unit 307. In some embodiments, a coupling between guiding catheter receiving unit 309 and microcatheter receiving unit 307 includes a junction 313 (optionally, a Y shaped junction). Optionally, a Y junction enables injection of materials (e.g. fluids) such as a contrast agent into the lumen of a guiding catheter 315 received within the unit. Optionally, a Y junction functions as mechanical support.

It is noted that in some embodiments, Y-shaped junctions may be generally positioned at points of engagement between tools and/or at tool openings, for potentially providing continuous washing of the inner lumen of the tool, such as to reduce or prevent formation of clots inside the lumen.

In some embodiments, guiding catheter receiving unit 309 includes a rail 310, optionally extending distally from juncture 313, on which the guiding catheter held by the unit can be moved distally and/or proximally, for example to an distance of between 10 mm –30 mm, 5 mm-15 mm, 1 mm-50 mm or intermediate, longer or shorter distance. In some embodiments, movement of the guiding catheter along the rail is by a leadscrew mechanism 302. In some embodiments, linear movement of the guiding catheter is by movement along the rail and/or by axial translation of the assembled system as a whole, such as relative to a mounting. The extent of linear movement may range up to the entire operable length of the guiding catheter.

In some embodiments, a sealer 312 is mounted at a position which prevents fluids from flowing proximally and into the system units.

In some embodiments, the guiding catheter unit comprises a rotational actuator 314 (e.g. a gear) configured for axially rotating the guiding catheter. Optionally, rotation is driven by a motor integrated inside the unit and/or by a gear interfacing with the system base, which encases one or more motors.

In some embodiments, during operation, the guiding catheter is advanced into a final location manually, and the guiding catheter unit provides for fine-tuning of the guiding catheter position, by a short distance linear advancement and/or retraction of the guiding catheter.

In some embodiments, a tool receiving unit (such as 305, 307) comprises a cover 317 sized and positioned to overlie the tool received within the unit and optionally maintain hold of the tool inside the unit (e.g. prevent the tool from being unintentionally pulled out).

In some embodiments, a tool is loaded onto a unit by insertion of the tool into a designated slot, for example slot 318 in the guidewire receiving unit 305 and slot 319 in the microcatheter receiving unit. In some embodiments, the slot extends longitudinally across a face of the housing (optionally, a top face). In some embodiments, the slot is formed in a longitudinal shaft 320. In some embodiments, loading is by manually grasping an elongate segment of the tool, and feeding the elongate segment into the slot.

In some embodiments, one or more tool moving elements such as wheels (e.g. wheels 321 of unit 305 and wheels 322 of unit 307) contact the tool once the tool is fully received within the slot. In some embodiments, the wheels are positioned opposite each other across the short dimension of the slot. Optionally, a spring based mechanism (not shown) spaces the wheels slightly away from the slot during insertion of the tool, and then moves the wheels into a position in which they operably engage the tool received within the slot. In some embodiments, opening of the cover 317 actuates the spring based mechanism to space the wheels apart, and closing of the cover moves the wheels into engagement with the tool.

A potential advantage of a slot through which the tool is loaded being configured on an outer face of a housing of a tool receiving unit, where the slot remains accessible even when the system is fully assembled, may include that a tool can be easily inserted, removed, or replaced, even during operation. In an example, if manual operation of a tool is required during the procedure, the tool can be easily removed from the accessible slot without removing the tool from the patient body.

Referring now to the tools operated by the system: in some embodiments, a guidewire 331 is manually inserted into a lumen of a microcatheter 335. In some embodiments, a free end of guidewire 331 is received within slot 317 of the guidewire receiving unit 305. Optionally, a proximal end of the guidewire is first inserted into torquer unit 311, and the guidewire is then turned (e.g. by a U shape curve) to fit within slot 317, extending in a distal to proximal direction. In some embodiments, the guidewire receiving unit includes a holder 333 extending from an exit end of the unit. Optionally, the holder comprises one or more sensors, such as an optical sensor, for indicating presence of the guidewire (for example, when the guidewire is in the holder, light is blocked by it, and when the guidewire is pulled out, light is no longer blocked. This change is then detected by the optical sensor). Other examples of sensors may include a magnetic sensor, a proximity (e.g. distance) sensor, a membrane sensor configured to sense contact, proximity, friction and/or other.

In some embodiments, upon exiting the holder 333, the guidewire continuously extends into an inner lumen of the microcatheter 335 into which it has been pre-threaded. The microcatheter is then fitted within slot 319 of the microcatheter receiving unit 307, extending in a proximal to distal direction throughout the slot, defining a U shaped curve with respect to the position of holder 333.

At a distal end of the microcatheter unit, microcatheter 335 (along with guidewire 331 extending within it) is then threaded into a lumen of the guiding catheter 315. The guiding catheter (including the microcatheter and guidewire inside it) may then be advanced into the patient body, for example into a blood vessel.

A potential advantage of the "winding" of tools (such as by the U shaped curves of a tool, where a tool enters the assembled system through a first end, exits the system in a second opposite end, and is then curved to re-enter the system in the second end, and then exits through the first end) may include that operation mechanisms (such as of the tool receiving units) may be aligned side by side (e.g. parallel to each other), allowing to minimize the overall system size.

Another potential advantage may include having more than one "manipulation location" for each tool, as the tool passes twice through the system.

In some embodiments, following the curve, the tool does not pass through the same exact path, but travels along a path which is adjacent (e.g. parallel) to the first path.

In some embodiments, the guidewire is curved twice (for example, a first time when extending between the torquer unit and the slot of the guidewire receiving unit, and a second time when exiting the guidewire receiving unit and entering the microcatheter receiving unit (where the guidewire is within the lumen of the microcatheter).

In some embodiments, the microcatheter is curved once, between exit of the guidewire receiving unit and the entry to the microcatheter receiving unit.

In some embodiments, the microcatheter receiving unit is supplied with an extension for a microcatheter, which can be used to lengthen the microcatheter, for example used as the segment which extends at the curve between the exit of the guidewire receiving unit and the microcatheter receiving unit.

In some embodiments, during operation, wheels 321 linearly advance and/or retract guidewire 331 by roll of the wheels. Optionally, the wheels are positioned to grasp the guidewire therebetween. In some embodiments, shaft 320 is rotated (optionally with the wheels rotating with the shaft as a single assembly, changing an orientation of the wheels) to cause rotation of the guidewire received within the slot. In some embodiments, the slot is shaped so that a guidewire received therein is centralized with respect to the shaft. In such configuration, rotation of the shaft may rotate the guidewire about the guidewire long axis (which unites with the shaft long axis).

In some embodiments, wheels 322 of the microcatheter receiving unit advance and/or retract microcatheter 335. In some embodiments, a mechanism such as a leadscrew mechanism 302 of the guiding catheter unit linearly advances and/or retracts the guiding catheter.

In some embodiments, wheel actuation of two or more units is controlled (e.g. by the system controller, optionally configured in a remote control device) to ensure that tools move together, for example, that the guidewire moves along with the microcatheter, or, alternatively, that tools do not move together (e.g. one tool is advanced while the other remains in place). In some embodiments, rolls of wheels 322 of the microcatheter receiving unit 307 are counted (optionally to deduce a distance of advancement and/or retraction of the microcatheter), and then wheels 321 of the guidewire receiving unit are rolled accordingly.

In an example, to advance only microcatheter 335 without advancing the guide wire, wheels 322 are rolled to advance the microcatheter forward while wheels 321 are rolled in the opposite direction to advance the guidewire backwards.

In another example, when the entire system is moved (e.g. slides linearly on a mounting) for adjusting a position of the guiding catheter, the microcatheter may be driven linearly in the opposite direction to compensate for the movement.

In another example, injection of a material (e.g. a contrast agent, a medicament, saline and/or other fluids) into the lumen of the microcatheter may require retracting the guidewire backwards, due to the small size of the microcatheter lumen. In such situation, before injection, wheels 321 may be actuated to retract the guide wire from within the lumen of the microcatheter.

FIGS. 4A-B are an isometric view and a side view of a modular robotic surgical system positioned with respect to a patient, according to some embodiments.

In some embodiments, an assembled modular robotic system 401 (including for example a motor base and a plurality of tool-receiving units, for example as described herein) is positioned with respect to a patient 403, optionally, with respect to a surgical body entry point in the patient. The entry point may be selected from, but not limited to, the patient's groin (i.e., the femoral artery), arm (i.e., the radial artery) or neck (i.e., the jugular vein).

In some embodiments, system 401 is mounted onto a rigid fixture 405. In some embodiments, the fixture is placed and/or restrained to the patient body. Additionally or alternatively, the fixture is attached to the surgical bed.

In some embodiments, fixture 405 is adjustable to control one or more positioning parameters of system 401, for example: a height, an angle (e.g. an angle of insertion into the body entry point), and a distance from the patient (e.g. from the entry point). Optionally, fixture 405 includes a rail on which system 401 can slide to be advanced towards and/or retracted from the patient.

In some embodiments, fixture 405 is manually adjustable, for example via a plurality of adjustable knobs 407.

A potential advantage of a relatively small and compact system may include that the system can be positioned relatively close the patient (e.g. to the body entry point), for example, at a distance of less than 2 cm, 3 cm, 5 cm, 10 cm or intermediate, longer or shorter distance from the entry point.

FIGS. 5A-B are a side view (FIG. 5A) and an exploded view (FIG. 5B) of a modular robotic surgical system including a guide wire unit, a microcatheter unit, and a guiding catheter unit, according to some embodiments.

In the example shown, system 501 comprises a base 503; a mounting 505; a torquer unit 507, a guidewire receiving unit 509; a guidewire holder 511; a microcatheter receiving unit 513; a guiding catheter receiving unit 514 including a rail 515 and a leadscrew mechanism 517 for providing limited linear movement of the guiding catheter; a Y-shaped junction 519 at the attachment of the guiding catheter receiving unit to the base 503 and/or to the microcatheter receiving unit 513.

Also shown are a guidewire 521; a microcatheter 523 into which the guidewire is at least partially inserted; and a guiding catheter 524 into which the guidewire and microcatheter assembly are at least partially inserted.

In some embodiments, tool receiving units are operably coupled to the base. In some embodiments, the coupling is an interference coupling, for example a protrusion and a respective recess. In some embodiments, one or more mechanical elements (such as a gear, transmission elements) and/or electrical couplings protrude from a housing of the base and are received within a housing of the unit, for example where they operably engage tool moving elements (such as the wheels positioned adjacent the slot). Additionally or alternatively, one or more mechanical elements such as a gear, transmission elements) and/or electrical couplings protrude from a housing of the tool receiving unit and are received within a housing of the base, for example where they operably engage the motor gears.

In the example shown, a gear wheel 525 and two projecting knobs 527, 528 of motors extend upwards from a top face 529 of the housing of base 503. The gear and/or knobs are then received within respective recesses formed in an opposing (e.g. bottom face) of the tool receiving unit housing(s). For example, gear 525 and knob 527 fit within respective recesses of the housing of guidewire receiving unit 509; and knob 528 fits within a respective recess of the housing of the microcatheter receiving unit 513 (the respective recesses are not shown.) (As referred to herein, the gear wheel may be defined as the "first coupler" of an interface coupling pair between the base and the unit, and the recess in the unit may be defined as the "second coupler" of the interface coupling pair. Some embodiments may include an opposite arrangement in which the unit includes a protruding element (first coupler) and the base defines a respective recess (second coupler).) In some embodiments, the first and second couplers are arranged symmetrically about at least one corresponding axis of the unit and base, allowing the assembled unit to be attached and operated in one of two orientations that are 180 degrees in relation to one another. For example, a first coupler including a protrusion extending from the base may be received within one of two respective second couplers, oppositely located on a proximal and distal end of a long axis or the tool receiving unit.

In some embodiments, torquer unit 507 is attached to the base via a protrusion (e.g. a knob of a motor, not shown) extending from a lateral face 531 of base 503. In some embodiments, the motor driving rotation in the torquer unit is the same motor used for driving rotation of the guidewire in the guidewire receiving unit.

In some embodiments, tool receiving units are coupled to each other. Optionally, the coupling is an operable coupling (e.g. including motor or power transmission); additionally or alternatively, the coupling is for system constructions purposes, for example, for locking the units in a relative position with respect to each other.

FIG. 6A-C show a guidewire receiving unit (with an open cover (FIG. 6A, 6C) and a closed cover (FIG. 6B)), according to some embodiments.

In some embodiments, a tool receiving unit such as guidewire receiving unit 601 comprises a housing 603. In some embodiments, the housing is shaped and/or sized to be coupled to a base (not shown). Optionally, the unit housing length 605 such as measured along the long (proximal-distal) axis is shorter than or equal to the base length, for example length 605 is between 10-20 cm, 15-18 cm, 5-30 cm or intermediate, longer or shorter. Optionally, unit width 607 such as measured along an axis perpendicular to the long axis is smaller than or equal to the base width, for example width 607 is between 4-12 cm, 3-10 cm, 2-15 cm or intermediate, longer or shorter. In a specific embodiment, width 607 is smaller than or equal to a half of the width of the base, for example so as to allow two units (e.g. the guidewire receiving unit and the microcatheter receiving unit) to fit together onto the base.

In some embodiments, a single tool receiving unit (e.g. a guidewire receiving unit, a microcatheter receiving unit) weighs less than 400 grams, 300 grams, 700 grams or intermediate, higher or lower weight.

In some embodiments, housing 603 includes an elongate slot 609 through which the tool is received. Optionally, the slot extends along at least a portion of the long axis of the unit. In some embodiments, the slot is formed within a moveable (e.g. rotatable) elongate shaft 604.

In some embodiments, an indentation is formed at the two opposite ends of the slot. Optionally, the indentation enables interlocking with another tool-receiving unit such as another linearly aligned unit.

In some embodiments, housing 603 accommodates one or more tool moving elements, such as wheels 611. The tool moving elements are located such that they operably contact the tool received within the unit, for example, adjacent the slot (in this example, two wheels are located on opposite sides of the slot's width).

In some embodiments, the tool segment inserted into the slot includes an intermediate portion of the tool (i.e. not a most proximal tool segment and not a most distal tool segment), for example, a segment that is configured between 20%-80% of a total length of the tool. The length of the tool segment inserted into the slot comprises for example of 5%, 10%, 2%, 20% or intermediate, higher or lower percentage of a total length of the tool. For example, 10 cm in a tool having a total length of up to 300 cm.

In some embodiments, the unit includes a cover 613 configured to overlie the slot. In some embodiments, the cover is shaped to fit onto the unit without interfering with movement of the tool-moving elements. In this example, cover 613 includes a semi-circular protrusion 615 within which the wheels 611 are free to move. In some embodiments, protrusion 615 enables a change in wheel orientation.

In some embodiments, as can be better observed for example in FIG. 6C, a rotatable gear 618 is configured at an end of shaft 604, whereby rotation of gear 618 (such as by a gear extending from the base) rotates the shaft and the wheels as a single unit, thereby rotating the slot in which the guidewire is received.

In some embodiments, an integrated linear motor 616 is positioned below the wheels and is configured to rotate the wheels for example so as to actuate linear movement of the guidewire. Optionally, an electrical coupling such as by a slip ring supplies electrical current to the linear motor 616. Coupling by the slip ring may provide that for each rotational position of the shaft (and guidewire), the linear motor 616 will be supplied with electrical current.

In some embodiments, cover 613 includes an elongate protrusion 617 which is aligned with the slot when the cover is closed, for protecting the tool received within the slot, without interfering with movement of the tool. In some embodiments, protrusion 617 provides for shaft 604 to freely rotate about the shaft axis, thereby rotating the guidewire received within the slot and gripped by the wheels.

In some embodiments, (not shown), a unit includes two or more slots in which a corresponding two or more guidewires may be loaded. In such configuration, the unit may include (or be attached to a connector including) a junction, such as a Y-junction. Optionally, the two (or more) slots will join at the junction, so that the user may decide which of the guidewires to advance forward through the junction. In some embodiments, in a unit including two or more slots, each slot may be associated with its respective tool moving elements (e.g. wheels). Optionally, the multiple tool moving elements may still be driven by the same one or more motors of the base (such as used for driving a single-slot unit).

In some embodiments, two or more tool-receiving units of a same type (e.g. two guidewire receiving units) may be used. Optionally, the units are aligned side by side. In such configuration, a connector including a junction may be attached to both units at an exit-end of the units, leading to the attachment with the microcatheter, and the user may decide which tool (of which unit) to advance further.

In some embodiments, more than one unit drives movement of the same single tool. In an example, a first unit includes a mechanism for advancing and/or retracting the tool; and a second unit includes a mechanism for axially rotating the same tool. In another example, rotation of a tool (e.g. guidewire) is actuated both by wheels of the unit and by another unit such as by the torquer unit (shown for example in FIG. 3).

A potential advantage of applying rotation from two distanced points along the guidewire (e.g. one point at the torquer unit, another point at the guidewire receiving unit) may include improving traction allowing for better manipulation of the tool to induce rolling.

In some embodiments, a guidewire includes a handle at its proximal end which is received at the torquer unit, and the handle is rotated to induce rolling of the guidewire. Alternatively, the handle remains hanging so as not to interfere with rolling applied from a different point along the guidewire.

FIGS. 6D-E show a guidewire holder, shown at an isometric view (FIG. 6D) and a cross section view (FIG. 6E), according to some embodiments.

In some embodiments, holder 651 is attached to the guidewire receiving unit at an exit end of the unit, and defines a central channel 653 for the guidewire to pass through. In some embodiments, a fastener 655 is attached externally to the holder, including a sensor (schematically indicated by numeral 657) for determining whether the guidewire is within channel 653 or not. Additionally or alternatively, a sensor may be integrated inside the holder. Examples of sensors for providing an indication of whether a guidewire has been received within the holder may include an optical sensor, a magnetic sensor, a proximity sensor and the like.

In some embodiments, a rotatable knob 659 is configured at an exit of the holder for tightening the microcatheter in place.

FIGS. 7A-E are various views of a base of a modular robotic surgical system, according to some embodiments.

Figure 7A:
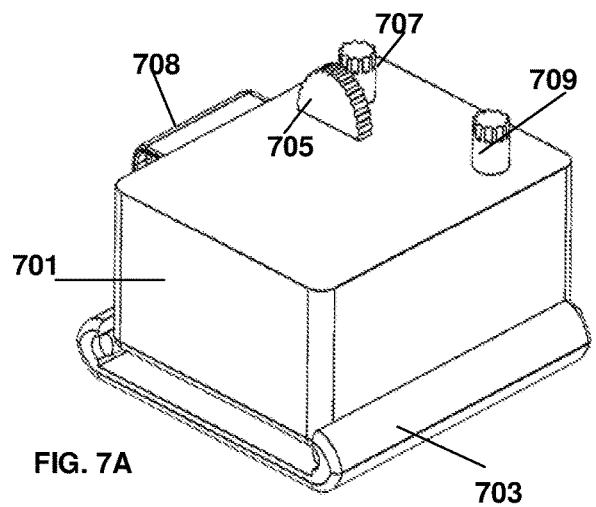
Figure 7B:
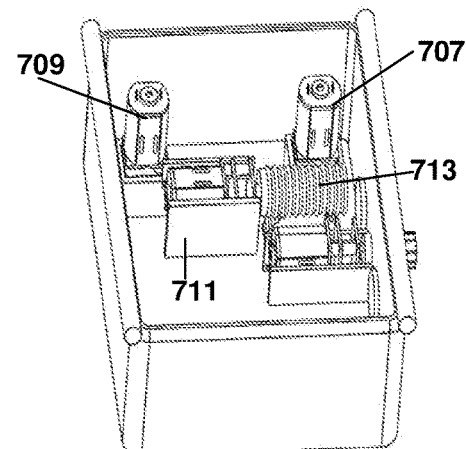
Figure 7C:
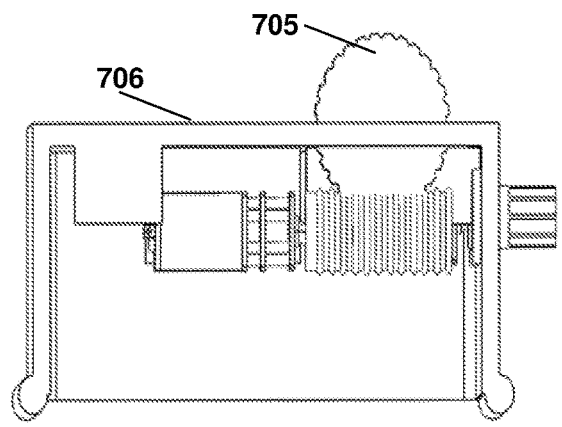
Figure 7D:
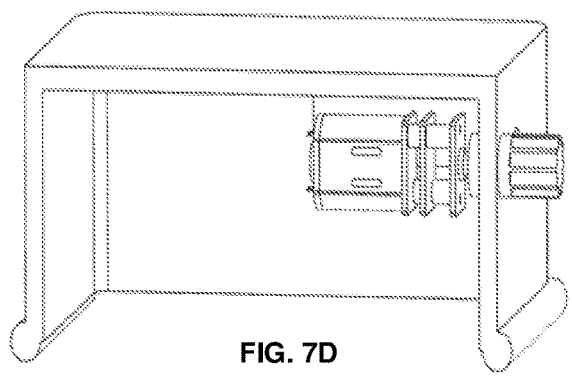
Figure 7E:
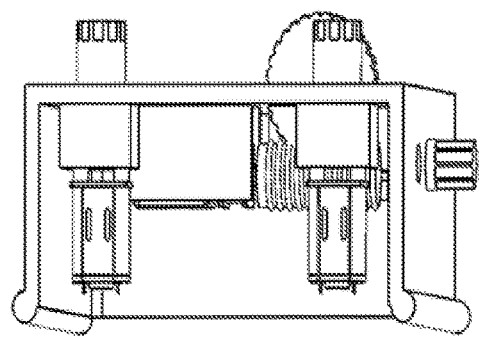
Figure 8A:
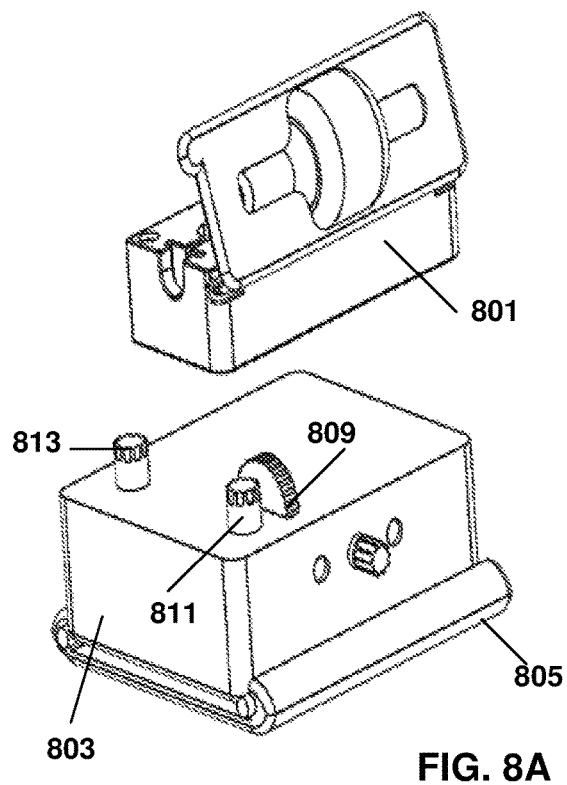
Figure 8B:
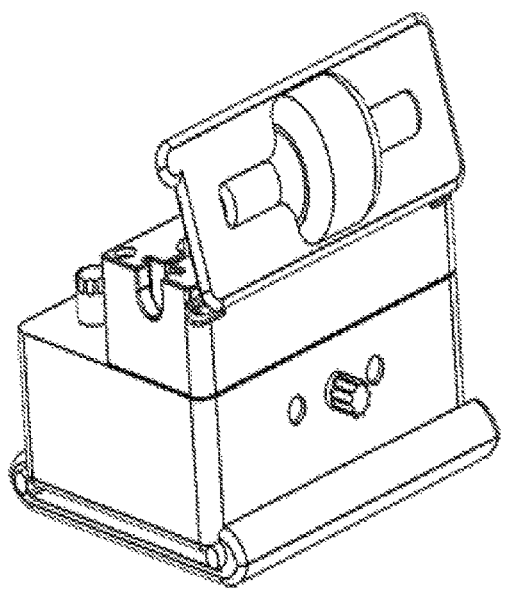
Figure 8C:
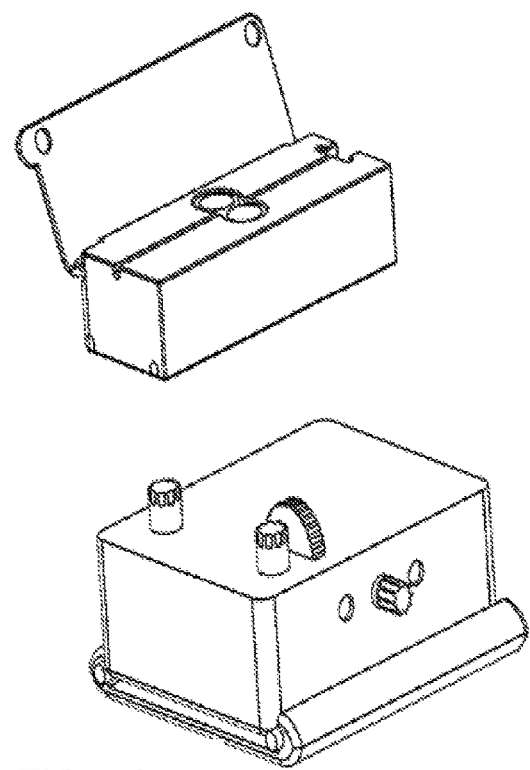
Figure 8D:
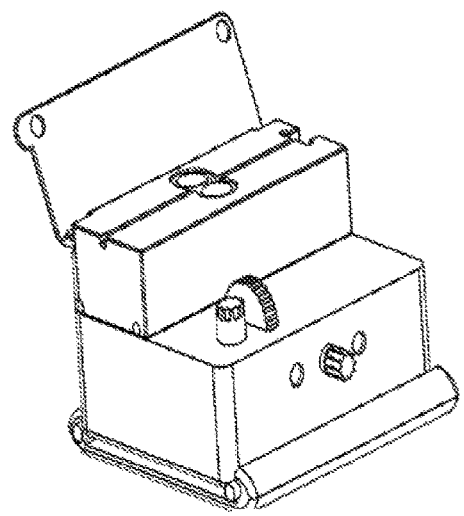

FIG. 7A is an isometric view of a base 701 seated on a mounting 703; FIG. 7B is an inside view of the base of FIG. 7A from the direction of the base bottom face; FIGS. 7C-7E are inside views of base 701, shown at different cross sections;

In some embodiments, one or more mechanical couplers, such as motor gears or associated transmission, protrude from the base to engage the tool-receiving units. In the example of FIG. 7A, the mechanical couplers include a gear wheel 705 for actuating rotational movement in a guidewire receiving unit; a motor 707 for actuating linear movement in a guidewire receiving unit; a motor 709 for actuating linear movement in a microcatheter receiving unit. In some embodiments, a torquer unit 708 attached for example to a lateral face of the base is configured to receive a guidewire proximal end or a guidewire handle (such as for driving rotation of the guidewire). In FIG. 7B, bottom portions of motors 707 and 709 are shown. Also shown is a motor 711 which rotates a worm gear 713, where gear wheel 705 is rotated by the worm gear. Further shown is a motor 715 for driving rotation in the torquer unit.

In some embodiments, as can be observed for example in FIG. 7C, gear wheel 705 extends on a plane that is substantially perpendicular to a plane of the top face 706 of the base housing. Having mechanical couplers such as the gear wheel protrude away from the base housing (and/or from the unit housing) is, in some cases, made possible due to that the system or parts of it are disposable, therefore having elements located externally to the housing of system components (which, in a reusable system, may lead to risk of contamination) is enabled.

In some embodiments, tool moving elements of a unit are driven by a designated motor of the base. Additionally or alternatively, tool moving elements of multiple units are driven by the same motor of the base.

FIGS. 7F-G are various views of another base configuration of a modular robotic surgical system, according to some embodiments. In this example, base 721 does not include a motor for driving linear movement in a guidewire receiving unit, and instead, the motor is configured in the guidewire receiving unit itself. In such configuration, an electrical coupling 723 (schematically shown in FIG. 7G) is provided, for example in the form of a slip ring, for supplying current to the motor within the unit.

FIG. 7H shows an example of a tool-receiving unit housing 731 configured to engage a base for example as shown in FIG. 7G. For example, a guidewire receiving unit. In some embodiments, as shown, the unit includes an interface for attaching to the base. In some embodiments, the interface comprises a recess 733 which is shaped and located to receive at least a portion of gear wheel 705 inside, upon attachment of the unit to the base. In some embodiments, the interface includes an electrical coupling 735 for connecting to the electrical coupling 723 of the base. In some embodiments, the interface to the base is located on a face of the unit housing which is opposite a slot in which the tool is received. Alternatively, the interface to the base may be located at a different face of the housing and/or at more than one face.

FIGS. 8A-D show attachment of a guidewire unit 801 onto a base 803 seated on a mounting 805 (FIGS. 8A-B) and attachment of a microcatheter unit 807 onto a base 803 seated on a mounting 805 (FIGS. 8C-D), according to some embodiments.

As shown in this example, a gear wheel 809 protrudes from the base to be fitted within the housing of guidewire unit 801, for driving rotation of the guidewire; a motor 811 protrudes from the base to be fitted within the housing of guidewire unit 801, for driving linear movement of the guidewire; and a motor 813 protrudes from the base to be fitted within the housing of the microcatheter unit 807, to drive linear movement of the microcatheter.

FIGS. 9A-B are isometric views of an assembled modular robotic surgical system 901, shown at FIG. 9A without a guidewire holder and at FIG. 9B with a guidewire holder 905 protruding from an exit end of the guidewire receiving unit, according to some embodiments.

In some embodiments, at a position of a junction (e.g. a Y-junction or a T-junction, as shown), one or more selector knobs 904 are used for regulating fluid flow through the junction.

FIGS. 10A-B are isometric views of an assembled modular robotic surgical system, shown without inserted tools (FIG. 10A) and with inserted tools (FIG. 10B), according to some embodiments.

In the example of FIGS. 10A-B, an assembled system 1001 includes the following system components: A base 1003 seared on a mounting 1002; a guidewire receiving unit 1005 and a microcatheter receiving unit 1007 mounted onto the top face of the base (both units shown with open covers); a guidewire holder 1009 extending in a proximal direction from an exit end of the guidewire receiving unit 1005, the holder being connected, at a proximal end, to a junction (port) 1011 enabling injection of materials into the lumen of a microcatheter; a guiding catheter receiving unit 1013 extending in a distal direction from the microcatheter receiving unit 1007, and including: a sealer 1015, an injection port 1017, and a rotation actuator (e.g. a motor and a rotating gear 1019). In some embodiments, junction (port) 1011 is integrated with the receiving unit.

FIGS. 11A-C show a guiding catheter receiving unit 1101, according to some embodiments. In some embodiments, the guiding catheter receiving unit includes a sealer 1103 which prevents entry of fluids in the proximal direction (e.g. into the system units). In some embodiments, the guiding catheter receiving unit includes a mechanism for linear movement of the guiding catheter, for example, a leadscrew mechanism 1105. In some embodiments, a motor (for example housing within the unit) actuates rotation of the leadscrew, generating advancement (or retraction) of the guiding catheter. The guiding catheter is shown at various positions—from a most proximal position (FIG. 11A) to a most distal position (FIG. 11C). In some embodiments, the leadscrew mechanism is configured for advancing and/or retracting the guiding catheter a linear distance 1107 (see FIG. 11C) of between 1-3 cm, 2-10 cm, 0.5-1 cm or intermediate, longer or shorter distance.

FIGS. 12A-D are several views of a modular robotic surgical system 1201 configured for use with a "rapid exchange" catheter, according to some embodiments.

In some embodiments, the modular system can be assembled for use with a rapid exchange catheter. In such configuration, the system is structured to independently drive movement of a guidewire and microcatheter (separately from each other), until reaching a junction in which they are joined.

In the example of FIGS. 12A-D, a guidewire 1203 extends from a torquer unit 1205 (mounted in this example on a lateral face of base 1207) and into the designated slot of a guidewire receiving unit 1209. A rapid exchange type microcatheter 1211 is independently placed within the designed slot of a microcatheter receiving unit 1213. Both the microcatheter and the guidewire are then advanced into channels of a Y-junction 1215, and join each other at the uniting point 1217 of the Y-junction. (Some embodiments may include a T-junction or any other configuration suitable to bring the tools via separate paths to then join each other at more distal position).

In some embodiments, the assembly of the guidewire and microcatheter is then advanced into the lumen of a guiding catheter 1219, held by a guiding catheter receiving unit 1221.

A potential advantage of independently driving movement of the guidewire and microcatheter may include that each can be individually controlled until reaching the uniting point. This may reduce the need to perform "compensation" movements of the guidewire and/or microcatheter with respect to each other, which may be required when both are driven together in an assembled configuration (such as when the guidewire is within the microcatheter lumen in the position of the tool moving elements of the unit, where the tool is manipulated). In a system configured for use with a rapid exchange catheter, manipulation of the tool (such as by tool moving elements of the unit) occurs proximally to the engagement of the guidewire and the rapid exchange catheter. This may provide for individually manipulating each of the tools.

Another potential advantage of using a rapid exchange catheter, which commonly has a thinner more proximal wire portion and a wider more distal "lumen" portion may include that manipulation of the thinner more proximal wire portion may be easier than manipulating a standard microcatheter.

Another potential advantage of using a rapid exchange catheter may include facilitating removal and/or replacement of a guidewire used with the rapid exchange catheter, since in the system configuration for use with a rapid exchange catheter there is no need to pass the guidewire during its withdrawal through a microcatheter receiving unit.

In some embodiments, there is more than one available configuration for attaching a unit is to the base and/or to other unit(s). Optionally, changing an attachment configuration also changes functionality of a unit. In an example, a guidewire unit can be rotated 180 degrees (relative to a basic configuration in which a standard microcatheter is used with the guidewire) for adapting to a configuration in which the guidewire is used with a rapid exchange catheter. In some embodiments, a unit can be rotated between available configurations about the unit's linear axis (for example so that an end face of the unit which previously faced a proximal direction now faces distally, and vice versa).

Figure 12A:
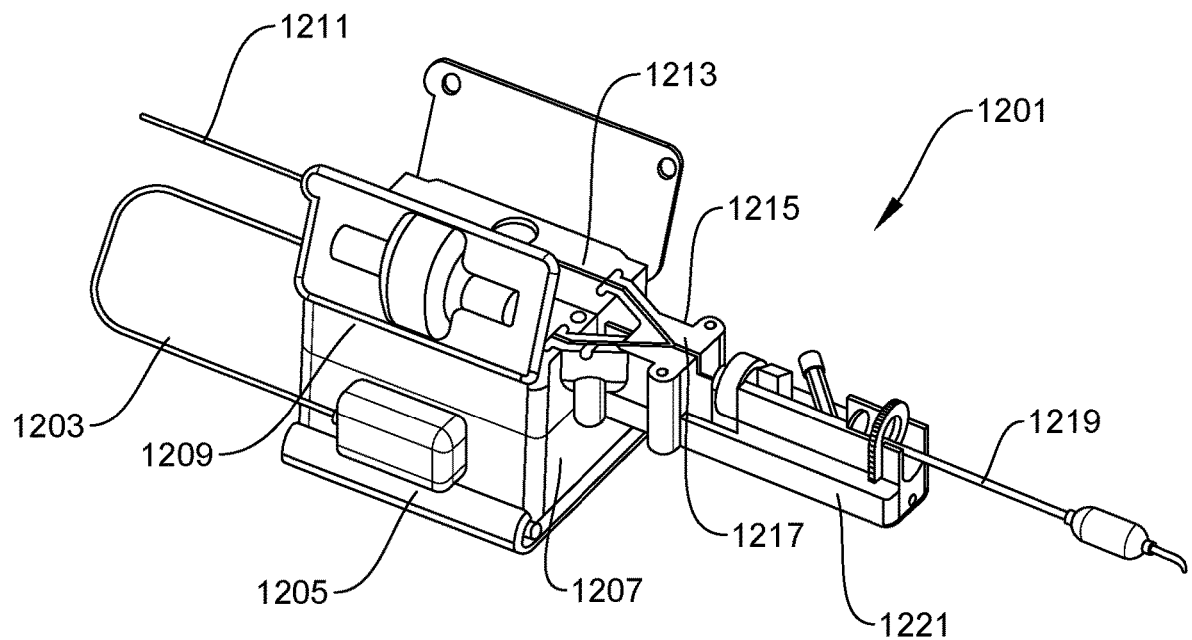
Figure 12B:
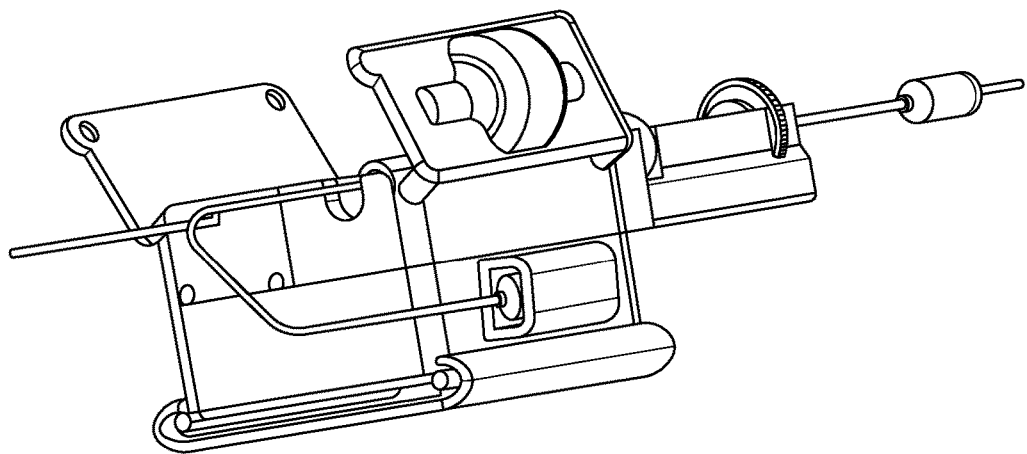
Figure 12C:
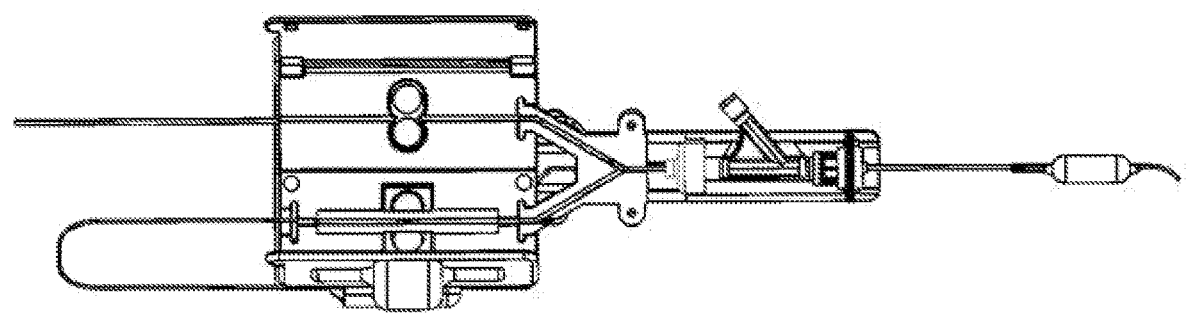
Figure 12D:
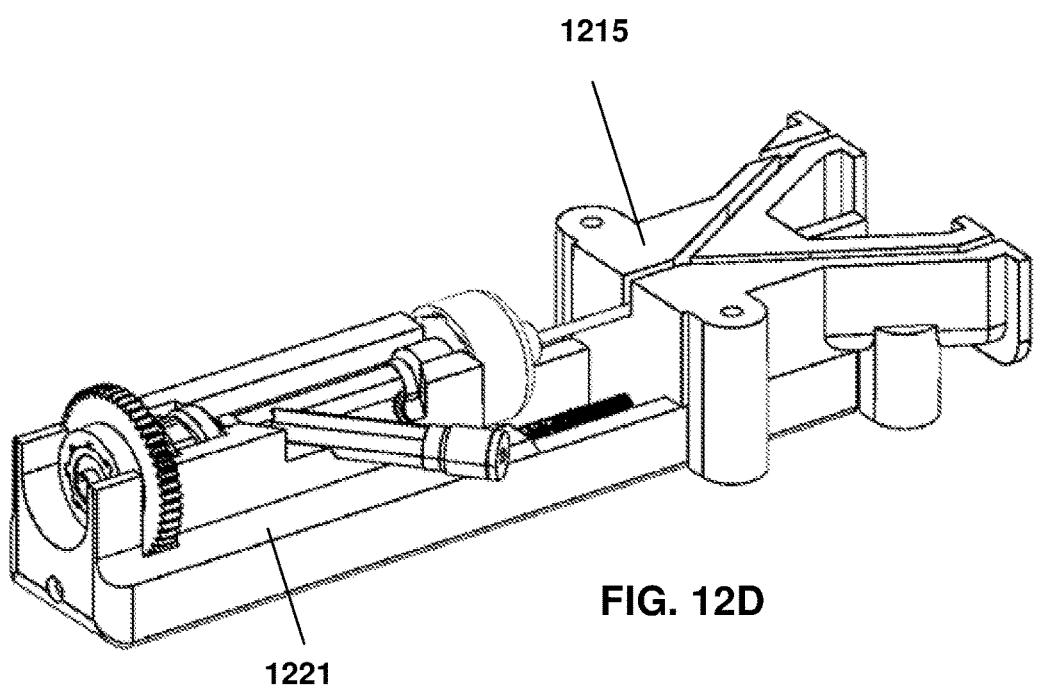

FIG. 12A shows an isometric view of the system; FIG. 12B shows a back view (in a proximal to distal direction) of the system; FIG. 12C shows a top view of the system; and FIG. 12D shows an enlarged view of the Y-junction 1215 and the guiding catheter receiving unit 1221 extending distally from the Y-junction.

FIGS. 13A-D are examples of a remote control device for controlling a modular robotic surgical system, according to some embodiments.

In some embodiments, the remote control device is shaped to be manually held by a user, e.g. a physician. Optionally, the remote control device is lightweight and small enough to be held by the user without blocking the user's view of visual aids such as a screen showing the results of imaging during operation. In some embodiments, the remote control device includes one or more portions shaped to be gripped by the user palm and/or engaged by the user's fingers.

In some embodiments, the remote control device communicates with the modular robotic system. In some embodiments, the communication is wireless, performed for example via Wi-Fi, infrared, Bluetooth, RF, and/or other wireless modules.

In some embodiments, the remote control device includes or is in communication with a controller of the modular robotic system. In some embodiments, maneuvering of tools received by the system is performed via the remote control device. Examples of tool movements and/or other operational manipulations of the tools which are controlled by the remote control device may include: linear advancement and/or retraction of a tool; axial rotation of a tool; control of a tool distal tip; speed of movement; control of unique tool functions (e.g. inflation/deflation of a balloon in a balloon catheter, stent deployment and/or advancement), and/or other tool manipulation.

Other functions which may be controlled via the remote control device include, for example: automated injection of materials (e.g. contrast agents, washing solutions) into and through a tool lumen; linear and/or angular movement of the assembled system as a whole (e.g. sliding of the assembled system relative to a mounting); safety stop of the system; on/off actuation of the system; supply of electrical power to the system or to specific components; and/or other system functions.

FIGS. 13A-B show a first example of a remote control device 1301, and FIGS. 13C-D show a second example of a remote control device 1303. In some embodiments, the device includes interfaces in the form of one or more of: push buttons 1305, joystick handles 1307, manual sliders 1309, rotating knobs, 1311 and the like.

In some embodiments, the remote control device is modular. Optionally, specific buttons and/or add-on interfaces are selectively attached (and/or are uncovered to enable their use) depending on the selected system configuration. For example, buttons for controlling movement of a guiding catheter (when a guiding catheter receiving unit has been attached on the system) are exposed for use only when required (e.g. are positioned under a removable or movable cover). In another example, an interface for controlling injection of materials through one or more system junctions is attached to the remote control device and/or uncovered for use upon need.

The remote control device may be operated at a distance from the system. Optionally, the remote control device is operated by a surgeon located in a different room.

FIGS. 14A-B schematically illustrate an assembly of a guidewire 1401; a microcatheter 1403; and guiding catheter 1405, according to some embodiments.

In some embodiments, the guidewire 1401 is at least partially inserted into the lumen of the microcatheter 1403, and the assembled guidewire and microcatheter are then advanced into the lumen of the guiding catheter 1405.

In some embodiments, an inner diameter of the microcatheter is only slightly larger than an outer diameter of the guidewire, for example being approximately 0.0254 mm larger, 0.127 mm larger, 0.254 mm larger or intermediate, larger or smaller size. In some embodiments, the inner diameter of the guiding catheter is larger than the outer diameter of the microcatheter, for example being approximately 0.05 mm, 0.01 mm, 0.1 mm larger or intermediate, larger or smaller size.

Exemplary tool sizes may include:
A guidewire having a dimeter of 0.18-1 mm;
A microcatheter having a diameter of 2-3 FR;
A guiding catheter having a diameter of 3-9 FR.

FIGS. 15A-D schematically illustrate various arrangements of a base and tool receiving units, according to some embodiments.

In some embodiments, one or more tool receiving units 1501 are operably coupleable to a base 1503. Optionally, units are attached on a top face of the base, as shown for example in FIG. 15A; additionally or alternatively, units are attached on a bottom face of the base, as shown for example in FIG. 15B; additionally or alternatively, units are attached on a lateral face of the base, as shown for example in FIG. 15C; additionally or alternatively, units are attached on opposing faces of the base, for example on opposing lateral faces, as shown for example in FIG. 15D.

In some embodiments, unit 1501 is aligned with respect to the base, for example such that the unit does not protrude, in cross section, beyond three faces of the base (in the example of a rectangular/square cross section base).

In some embodiments, one or more of: magnets 1505; interfering elements 1507 (e.g. a protrusion received within a respective recess); and/or external connectors 1509 assist in aligning and/or coupling and/or locking the unit to the base. In some embodiments, the interfering elements serve as operational components of the system, such as gears and/or transmission which transfer actuation force from the base to the tool moving elements of the unit. In an example, a mechanical coupler (e.g. a gear) protrudes from the base housing and extends into a designated recess in the unit housing; additionally or alternatively, a mechanical coupler (e.g. a gear) protrudes from the unit housing and is received within a designated recess in the base.

In some embodiments, the base and unit include a mechanical keying pattern and/or latches and/or snap-fit mechanism which ensures fitting of a unit onto the base and/or contributes to alignment of the unit relative to the base.

In some embodiments, an electronic coupling 1511 is provided. Such coupling may include an electrical connection, for example for supplying current to components of the tool receiving unit.

In some embodiments, identification of a unit is performed at the interface between the base and unit, for example to ensure that a correct unit is being attached to the base. For example, via an RFID tag which is read by the base.

FIGS. 16A-B show a slidable attachment of a guiding catheter unit, according to some embodiments.

In some embodiments, modular units of the device are configured to attach to each other and/or attach to the base via a slidable attachment, for example, an attachment including a rail. Optionally, a unit can be approximated or distanced from the base by sliding on the rail.

In the examples shown, a guiding catheter unit 1601 is configured to attach to a base (see 1600 in FIG. 16A, 1602 in FIG. 16B) by sliding on a rail 1606.

In some embodiments, as shown in this example, the base is configured to drive movement of a guidewire 1607 and optionally of a microcatheter 1609 within which the guidewire is received. In some embodiments, the microcatheter (along with the guidewire extending inside it) is received within a lumen of a guiding catheter 1611 driven by the guiding catheter unit.

In some embodiments, the guiding catheter unit attaches to a housing of the base in a manner in which a microcatheter existing the housing (such as via an aperture 1605) enters a lumen of a guiding catheter loaded onto the guiding catheter unit.

In some embodiments, rail 1606 moveably couples the guiding catheter unit 1601 to one or more motors located inside the base housing, for example so that a motor drives back and forth movement of the unit for moving the guiding catheter.

In some embodiments, the guiding catheter unit is configured to drive linear movement and/or rotational movement (i.e. roll) of the guiding catheter. Optionally, the guiding catheter driving mechanism is configured for driving linear movement of the guiding catheter within a selected distance range, for example, to advance and/or retract the catheter a distance of 3 cm, 5 cm, 10 cm, or intermediate, longer or shorter distance. In some embodiments, this provides for fine tuning of a position of a guiding catheter previously inserted into the patient.

FIGS. 17A-B illustrate moving units for linear advancement and/or rotational movement of the surgical tool, according to some embodiments. In some embodiments, as shown in FIGS. 17A-17B, linear and/or rotational movement of the guidewire may be generated by means of piezoelectric actuators or motors. Piezoelectric elements are composed of ceramic material which changes its geometric dimensions as a function of the applied voltage. Piezoelectric elements may enable activation at high frequencies, e.g., 50-150 kHz, and they can produce relatively large forces, which are linearly correlated to the degree of lengthening of the element (stroke). A potential advantage of using piezoelectric actuators in an automated medical device may include that activation of the piezoelectric elements does not generate a magnetic field, which is undesirable in some medical applications. Further, piezoelectric actuators are MRI compatible. In some embodiments, other actuator (e.g.

motor) types may be used, for example, electromagnetic actuators (solenoid), DC motors, stepper motors or AC motors.

According to some embodiments, the robotic device may include two modules (mechanisms): a first module for generating linear movement and a second module for generating rotational movement. Optionally, each module allows its associated movement type, i.e., linear and rotational, to be generated independently of the other. In some embodiments, a combined movement, i.e., simultaneous rotation and linear advancement, may be generated by activating the two modules in an ordered or alternate manner.

In some embodiments, the linear module may be in the form of an inchworm motor, and it may comprise three piezoelectric actuators, as shown for example in FIG. 17A. Piezo actuators 1701 and 1703 are used to grip the tool 1704 (e.g., a guidewire), by extending (lengthening) and relaxing (shortening) along the vertical axis when powered, and motion is achieved by piezo actuator 1702 lengthening and shortening along the horizontal axis when powered. In some embodiments, piezo actuator 1701 and/or 1703, may include a single actuator which presses the guidewire 1704 against a static element, when extending, to grip the guidewire 1704. In other embodiments, piezo actuators 1701 and/or 1703 are de facto a pair of piezo actuators, positioned on opposite sides of the guidewire 1704, such that both extend and relax to grip and release, respectively, the guidewire 1704.

In some embodiments, the actuation process of the linear portion is a cyclic process. In order to move the tool 1704 from left to right, for example, piezo actuator 1703, which is the forward clutch piezo in this example, is first extended so as to grip the tool, for example as shown in FIG. 17A. Next, piezo actuator 1702, the lateral piezo, is extended, resulting in piezo actuator 1703, together with the tool, moving a small distance to the right.

It should be noted that in some embodiments, the center of piezo actuator 1702 is fixated, such that when power is supplied to piezo actuator 1702, its extension is symmetrical to both sides, left and right. Since at this stage of the process piezo actuator 1701, which is the aft clutch piezo in this example, is in a relaxed state, and does not grip the tool, the tool, which is gripped by piezo actuator 1703, moves to the right. Next, piezo actuator 1701 is extended so as to grip the tool, followed by the relaxation of piezo actuator 1703, so as to release its grip of the tool. Next, piezo actuator 1702 is relaxed. Next, piezo actuator 1703 is extended to re-grip the tool, followed by the relaxation of piezo actuator 1701.

As shown in FIG. 17B, the rotational module of the device may include a pair of piezo actuators 1706, 1707, which contact the tool 1708 on opposite sides, parallel to one another. In some embodiments, extending the two piezo actuators in opposite directions 1709A and 1709B causes the tool to rotate.

In some embodiments, at least one of the clutch piezo actuators/pairs, i.e., piezo actuator 1701 and/or piezo actuator 1703, may be part of the rotational module of the device, as well as of the linear module of the device, as described above. In other embodiments, an additional pair of piezo actuators may be used for rotating the guidewire.

Reference is now made to FIG. 18, depicting a schematic illustration of an exemplary device capable of imparting both linear and rotational motion on a medical tool, according to some embodiments.

In some embodiments, the linear motion may be achieved in an inchworm manner using piezo motors 1801, 1802 and 1803, essentially as described above with respect of FIGS. 17A-17B, but with additional piezo motors 1804 and 1805 serving as clutches which are moved toward and away from the medical tool (shown as guidewire 408) by piezo motor 1803. In some embodiments, in order to rotate the guidewire clockwise ("CW"), for example, piezo motor 1803 is relaxed/contracted, such that it moves piezo motors 1804 and 1805 toward the guidewire 1808, until they grip the guidewire, at opposite sides. Piezo motor 1805 is then extended (moved downward), while piezo motor 1804 is simultaneously relaxed/contracted (moved upward), causing the guidewire to rotate. Piezo motor 1801 is then extended, so as to grip the guidewire, and piezo motor 1803 is extended, so as to release the grip of the guidewire by moving piezo motors 1804 and 1805 away from the guidewire, to their original position.

In alternative embodiments, an additional piezo motor may be coupled to one of piezo motors 1804 and 1805, instead of piezo motor 1803, to move it toward and away from the guidewire. In such embodiments, rotation of the guidewire may be achieved by both piezo motors 1804 and 1805 extending (or contracting), in opposite directions. The utilized piezo actuator/s may be, for example, the PICMA® Monolithic Multilayer PZT Actuator, manufactured by PI Ceramic GmbH, Germany. In some embodiments, the rotating piezo actuators can rotate the entire linear advancement assembly.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A modular robotic surgical system comprising:
    a base;
    a plurality of tool-receiver units arranged as separate units, each tool-receiver unit operable to move an elongate surgical tool received therein;
    each of said units independently and interchangeably attachable to said base via an interface which transfers one or more of: mechanical driving force for driving movement of said elongate surgical tool received within each of said units; electrical power supply to one or more components of said unit which drive movement of said elongate surgical tool received within each of said units; and data for controlling movement of said elongate surgical tool received within each of said units by said unit;
    wherein each of said tool-receiver units comprises a slot configured to receive said elongate surgical tool, and a plurality of tool-moving elements located adjacent said slot; and
    wherein said tool-moving elements comprise a set of wheels positioned diametrically opposing said slot, said wheels positioned and configured to contact an elongate surgical tool received within said slot and for moving the tool.

2. The system according to claim 1, wherein said interface of each of said units comprises a plurality of interface coupling pairs, each coupling pair comprising a first coupler as part of said base and a second coupler as part of each of said tool-receiver units.

3. The system according to claim 1, wherein at least one of said tool-receiver units is configured to receive and drive movement of a single elongate surgical tool only.

4. The system according to claim 1, wherein at least two of said plurality of tool-receiver units are configured to receive and drive movement of a same elongate surgical tool.

5. The system according to claim 1, wherein said base comprises a housing including one or more motors.

6. The system according to claim 1, wherein the plurality of tool-receiver units comprising at least two tool-receiver units, and wherein said at least two tool-receiver units are configured to be aligned parallel to each other such that an elongate surgical tool received within a first tool-receiver unit curves into a U-shape when exiting the first tool-receiver unit and before entering the second tool-receiver unit.

7. The system according to claim 1, wherein the plurality of tool-receiver units comprising at least two tool-receiver units, wherein a single elongate surgical tool is moveable by said at least two tool-receiver units.

8. The system according to claim 2, wherein said first coupler comprises a mechanical coupler extending from within a housing of said base, and wherein said second coupler comprises a recess in a housing of each of said tool-receiver units into which said mechanical coupler extends, or vice versa;
    wherein said mechanical coupler comprises a gear wheel, said gear wheel being positioned and configured to drive movement of tool-moving elements of each of said tool-receiver units in response to actuation of one or more motors of said base.

9. The system according to claim 2, wherein said first and second couplers comprise interfacing electrical connections.

10. The system according to claim 2, including two or more coupling pairs which are symmetrically aligned to enable attachment of at least one tool-receiver unit and said base at a first orientation and a second orientation, wherein in the second orientation said tool-receiver unit is rotated 180 degrees relative to the first orientation.

11. The system according to claim 1, wherein said elongate surgical tool capable of being received in each of said plurality of tool-receiver units is selected from the group of: a guidewire, a microcatheter, a guiding catheter, an intermediate catheter, a "rapid exchange" catheter.

12. The system according to claim 1, further comprising at least one controller configured to coordinate actuation of tool-moving elements configured in each of said plurality of tool-receiver units; and
    wherein said tool-moving elements drive one or both of: linear advancement and retraction of an elongate surgical tool received within said tool-receiver unit; rotation of an elongate surgical tool received within said tool-receiver unit.

13. The system according to claim 1, wherein at least one of said tool-receiving units comprises one or more motors.

14. The system according to claim 1, wherein at least one of said tool-receiving units is configured to receive a handle of said elongate surgical tool.

15. The system according to claim 1, wherein said base is configured to drive at least one elongate surgical tool received therein.

16. A method of assembling and operating a modular robotic surgical system, comprising:
    selecting a system configuration according to a surgical procedure to take place;

assembling the system by operably attaching at least one tool-receiver unit configured to receive an elongate surgical tool onto a base, said base comprising at least one motor configured to drive movement of said elongate surgical tool;

positioning the assembled system with respect to a patient; and carrying out the surgical procedure by controlling movement of said elongate surgical tool within the body of the patient, said controlling comprising activating said at least one motor of said base;

wherein said attaching comprises coupling one or more interfaces between said at least one tool-receiver unit and said base; said one or more interfaces configured for transferring one or more of: mechanical driving force for driving movement of said elongate surgical tool; electrical power supply to one or more components of said unit which drive movement of said elongate surgical tool; and data for controlling movement of said elongate surgical tool by said unit;

wherein each of said tool-receiver units comprises a slot configured to receive said elongate surgical tool, and a plurality of tool-moving elements located adjacent said slot; wherein said assembling comprises inserting said elongate surgical tool in said slot; and wherein said tool-moving elements comprise a set of wheels positioned diametrically opposing said slot, said wheels positioned and configured to contact an elongate surgical tool received within said slot and for moving the tool.

17. The method according to claim 16, wherein said operably attaching comprises operably attaching at least two tool-receiver units onto said base, at least one of said tool-receiver units configured to receive only a single elongate surgical tool, thereby carrying out said surgical procedure by controlling movement of at least two elongate surgical tools.

18. The method according to claim 16, wherein said controlling movement comprises controlling at least one of: linear movement of said elongate surgical tool, rotational movement of said elongate surgical tool, and actuation of a distal tip of said elongate surgical tool, and wherein said elongate surgical tool is selected from the group of: a guidewire, a microcatheter, an intermediate catheter, a guiding catheter.

19. The method according to claim 16, wherein said controlling is performed using a remote control device which is in wireless communication with said system.

20. The method according to claim 16, wherein said controlling comprises automatically limiting movement or generating movement of at least one elongate surgical tool according to movement of at least one other elongate surgical tool.

21. The method according to claim 16, wherein said operably attaching includes directly attaching said at least one tool-receiver unit and said base without draping either one of said base or said at least one tool-receiver unit.

22. The method according to claim 16, further comprising operatively coupling a handle of said elongate surgical tool to at least one other tool-receiver unit.

* * * * *